US012678410B2

(12) United States Patent
Varga et al.

(10) Patent No.: US 12,678,410 B2
(45) Date of Patent: Jul. 14, 2026

(54) RESPIRATORY SYNCYTIAL VIRUS (RSV) POLYANHYDRIDE NANOPARTICLE VACCINE

(71) Applicant: University of Iowa Research Foundation, Iowa City, IA (US)

(72) Inventors: Steven M. Varga, Coralville, IA (US); Kevin L. Legge, North Liberty, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 1091 days.

(21) Appl. No.: 17/674,683

(22) Filed: Feb. 17, 2022

(65) Prior Publication Data

US 2023/0250431 A1    Aug. 10, 2023
US 2026/0096999 A9    Apr. 9, 2026

Related U.S. Application Data

(63) Continuation of application No. 16/666,214, filed on Oct. 28, 2019, now abandoned.

(60) Provisional application No. 62/752,006, filed on Oct. 29, 2018.

(51) Int. Cl.

| | |
|---|---|
| *A61K 31/713* | (2006.01) |
| *A61K 9/00* | (2006.01) |
| *A61K 9/51* | (2006.01) |
| *A61K 31/7105* | (2006.01) |
| *A61K 39/155* | (2006.01) |
| *A61K 39/39* | (2006.01) |
| *A61P 31/14* | (2006.01) |
| *C12N 7/00* | (2006.01) |
| *C12N 15/113* | (2010.01) |
| *A61K 39/00* | (2006.01) |

(52) U.S. Cl.

CPC .......... *A61K 9/5146* (2013.01); *A61K 9/0048* (2013.01); *A61K 31/7105* (2013.01); *A61K 31/713* (2013.01); *A61K 39/155* (2013.01); *A61K 39/39* (2013.01); *A61P 31/14* (2018.01); *C12N 7/00* (2013.01); *C12N 15/113* (2013.01); *C12N 15/1136* (2013.01); *A61K 2039/55561* (2013.01); *C12N 2310/14* (2013.01); *C12N 2310/321* (2013.01); *C12N 2320/30* (2013.01); *C12N 2320/31* (2013.01); *C12N 2760/18534* (2013.01)

(58) Field of Classification Search
None
See application file for complete search history.

(56) References Cited

U.S. PATENT DOCUMENTS

| | | | |
|---|---|---|---|
| 7,390,333 | B2 | 6/2008 | Dutta |
| 7,470,283 | B2 | 12/2008 | Dutta |
| 7,659,322 | B1 | 2/2010 | Vogel et al. |
| 7,858,093 | B1 | 12/2010 | Kipper et al. |
| 8,173,104 | B2 | 5/2012 | Kipper et al. |
| 8,449,916 | B1 | 5/2013 | Bellaire et al. |
| 9,060,975 | B2 | 6/2015 | de Haan et al. |
| 9,498,531 | B2 | 11/2016 | Corti |
| 9,963,500 | B2 | 5/2018 | Vora et al. |
| 10,017,543 | B2 | 7/2018 | Kwong et al. |
| 10,047,145 | B2 | 8/2018 | Corti |
| 10,072,071 | B2 | 9/2018 | Corti |
| 2013/0122032 | A1 | 5/2013 | Smith et al. |
| 2014/0107062 | A1 | 4/2014 | Shenoy |
| 2014/0141037 | A1 | 5/2014 | Swanson et al. |
| 2015/0030622 | A1 | 1/2015 | Marshall et al. |
| 2015/0216888 | A1 | 8/2015 | Bellaire et al. |
| 2016/0030146 | A1 | 2/2016 | Jones et al. |
| 2018/0179266 | A1 | 6/2018 | Saelens et al. |
| 2018/0237476 | A1 | 8/2018 | Swanson et al. |
| 2022/0193224 | A1* | 6/2022 | Oomens ............... A61K 39/155 |

FOREIGN PATENT DOCUMENTS

| | | |
|---|---|---|
| WO | 2008115641 A2 | 9/2008 |
| WO | 2010077717 A1 | 7/2010 |
| WO | 2015024668 A2 | 2/2015 |
| WO | 2015130584 A2 | 9/2015 |
| WO | 2017040387 A2 | 3/2017 |

OTHER PUBLICATIONS

McGill et al. Scientific Reports 2018, 8:3021 (Year: 2018).*
McLellan et al. Science 2013:vol. 342, Issue 6158, pp. 592-598 (Year: 2013).*
Wafa et al. Acta Biomaterialia vol. 50, pp. 417-427 (Year: 2017).*
Hancock et al. Vaccine vol. 19, Issue 32, Sep. 14, 2001, pp. 4874-4882 (Year: 2001).*
Joshi et al. Acta Biomaterialia vol. 9, Issue 3, Mar. 2013, pp. 5583-5589 (Year: 2013).*
Borchers et al. Clinic Rev Allerg Immunol (2013) 45:331-379 (Year: 2013).*
Anderson, L. et al., Strategic Priorities for Respiratory Syncytial Virus (RSV) Vaccine Development, Vaccine, 2013, 31:B209-B215.
Blais, N. et al., Characterization of Pre-F-GCN4t, a Modified Human Respiratory Syncytial Virus Fusion Protein Stabilized in a Noncleaved Prefusion Conformation, Journal of Virology, 2017, 91(13):e02437-16, pp. 1-18.

(Continued)

*Primary Examiner* — Shanon A. Foley
*Assistant Examiner* — Myron G Hill
(74) *Attorney, Agent, or Firm* — Quarles & Brady LLP

(57) ABSTRACT

Disclosed are compositions and methods for vaccinating susceptible individuals against infection by respiratory syncytial virus (RSV). The disclosed compositions include vaccine compositions comprising an effective amount of respiratory syncytial virus (RSV) F protein in a pre-fusion stabilized form and/or M protein incorporated into biodegradable polyanhydride polymer particles for inducing an immune response against RSV. The vaccine compositions also may include a suitable adjuvant.

20 Claims, 29 Drawing Sheets

Specification includes a Sequence Listing.

(56)        References Cited

OTHER PUBLICATIONS

Carrillo-Conde, B. et al., Chemistry-Dependent Adsorption of Serum Proteins onto Polyanhydride Microparticles Differentially Influences Dendritic Cell Uptake and Activation, Acta Biomaterialia, 2012, 8:3618-3628.

Joyce, M. et al., Iterative Structure-Based Improvement of a Fusion-Glycoprotein Vaccine Against RSV, Nature Structural & Molecular Biology, 2016, 23(9):811-820.

Krarup, A. et al., A Highly Stable Prefusion RSV F Vaccine Derived from Structural Analysis of the Fusion Mechanism, Nature Communications, 2015, 6:8143, pp. 1-12.

Lee, W. et al., Complete Genome Sequence of Human Respiratory Syncytial Virus Genotype A with a 72-nucleotide Duplication in the Attachment Protein G Gene, Journal of Virology, 2012, 86(24):13810-13811.

Morrison, T. et al., Subunit and Virus-Like Particle Vaccine Approaches for Respiratory Syncytial Virus, Current Topics in Microbiology and Immunology, 2013, 372:285-306.

Raghunandan, R. et al., An Insect Cell Derived Respiratory Syncytial Virus (RSV) F Nanoparticle Vaccine Induces Antigenic Site II Antibodies and Protects Against RSV Challenge in Cotton Rats by Active and Passive Immunization, Vaccine, 2014, 32(48):6485-6492.

Steff, A. et al., Pre-Fusion Rsv F Strongly Boosts Pre-Fusion Specific Neutralizing Responses in Cattle Pre-Exposed to Bovine RSV, Nature Communications, 2017, 8:1085, pp. 1-10.

Stephens, L. et al., Prefusion F-Based Polyanhydride Nanovaccine Induces Both Humoral and Cell-Mediated Immunity Resulting in Long-Lasting Protection Against Respiratory Syncytial Virus, Journal of Immunology, 2021, 206:2122-2134.

Stephens, L. et al., Long-Lasting Protection Induced by a Polyanhydride Nanovaccine Against Respiratory Syncytial Virus in an Outbred Mouse Model, Journal of Virology, 2022, 96(22):1-14.

* cited by examiner

C

RESPIRATORY SYNCYTIAL VIRUS (RSV) POLYANHYDRIDE NANOPARTICLE VACCINE

CROSS-REFERENCE TO RELATED PATENT APPLICATIONS

The present application is a continuation of U.S. application Ser. No. 16/666,214 filed on Oct. 28, 2019 and published as U.S. 2020/0129446 on Apr. 30, 2020, and which claims the benefit of priority under 35 U.S.C. § 119(e) to U.S. Provisional Application No. 62/752,006, filed on Oct. 29, 2018. The content of each of the above-referenced applications is incorporated herein by reference in its entirety.

SEQUENCE LISTING

This application contains, as a separate part of the disclosure, a Sequence Listing in computer readable form (filename: 139766.00096CON_SeqList.txt; Created: 25 Oct. 2019; 67,000 bytes), which is incorporated herein by reference in its entirety.

STATEMENT REGARDING FEDERALLY SPONSORED RESEARCH OR DEVELOPMENT

This invention was made with government support under AI124093 awarded by the National Institutes of Health. The government has certain rights in the invention.

BACKGROUND

The field of the invention relates to compositions and methods for inducing an immune response against respiratory syncytial virus (RSV). In particular, the field of the invention relates to compositions and methods for vaccinating susceptible individuals against infection by RSV by administering particulate vaccines comprising RSV structural components or variants thereof and optionally an adjuvant.

Respiratory syncytial virus (RSV) is the leading cause of lower respiratory infections in young children, resulting in 34 million new RSV infections each year, and approximately 125,000 hospitalizations annually in the United States alone. RSV reinfection is common in children, and even adults can be susceptible to repeated infection due to short-lived and incomplete protective immunity after natural infection. Especially vulnerable populations include premature babies, the elderly, people with heart or lung disease, and people with a very weak immune system. There are no effective vaccines for RSV, and work in the field has been slow since two children died during an RSV vaccine test in 1966.

RSV is an RNA virus with a genome that expresses eleven (11) known proteins. One of these, F protein, causes the virion membrane to fuse with the target cell's membrane. F proteins are targeted by antibodies after infection and are the major target for antiviral drug development. Fusion causes a confirmation change that obscures the major F antigenic site, site Ø. As such, RSV vaccines that induce immune response against Ø and other antigens of RSV such as M protein are desirable.

SUMMARY

Disclosed are compositions and methods for vaccinating susceptible individuals against infection by respiratory syncytial virus (RSV). The disclosed compositions include vaccine compositions comprising an effective amount of respiratory syncytial virus (RSV) F protein in a pre-fusion stabilized form and/or M protein incorporated into biodegradable polyanhydride polymer particles for inducing an immune response against RSV. The vaccine compositions also may include a suitable adjuvant.

Lungs and spleens were harvested on day 42 and analyzed by flow cytometry. Frequency of (A) activated (CD11a$^{hi}$CD49d$^{+}$) CD4 T cells and (B) activated) (CD11a$^{hi}$CD8$^{lo}$) CD8 T cells. Statistical significance was determined by 2-way ANOVA with Tukey's post hoc test. p<0.01, *p<0.001.

Figure 9:
Figure 9:
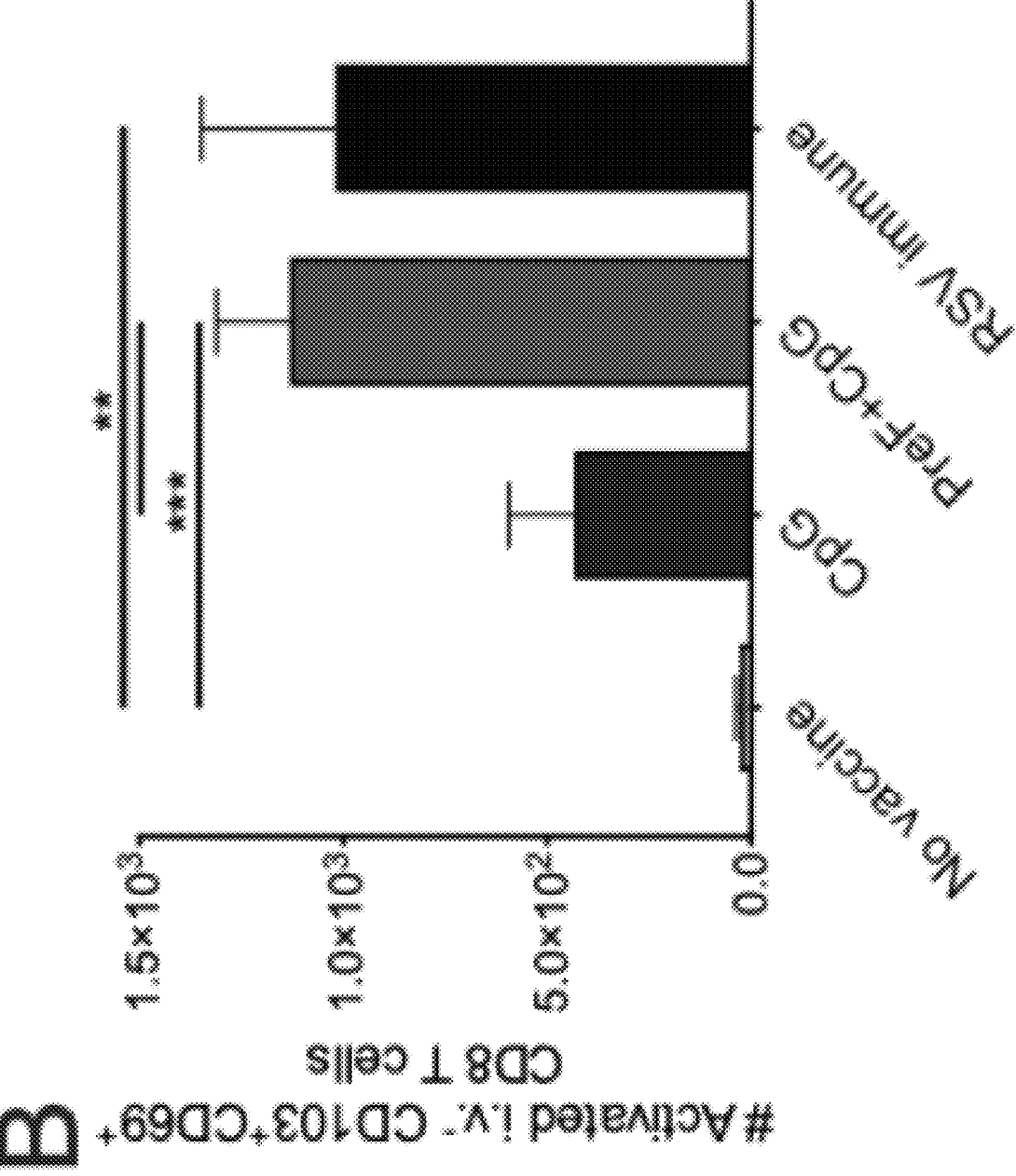
Figure 9:
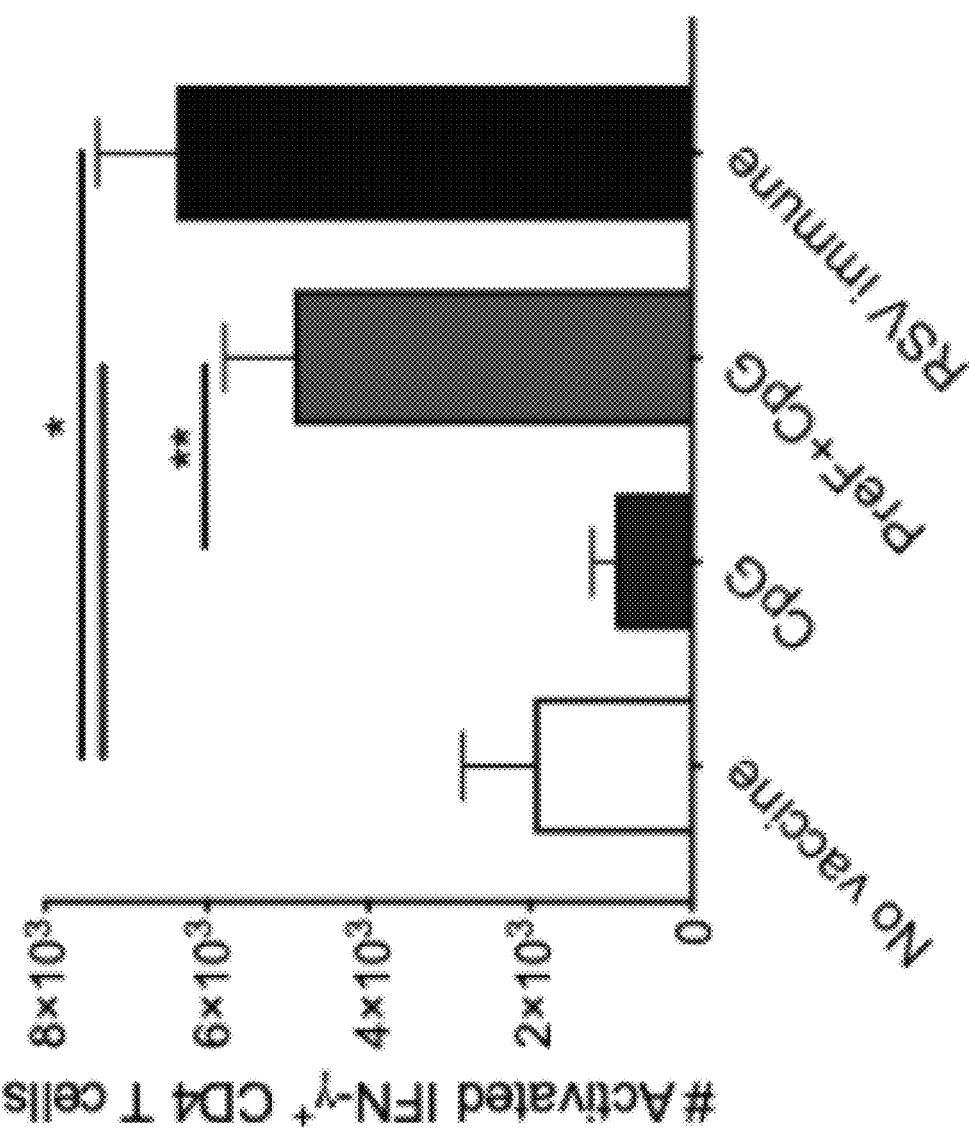
Figure 9:
Figure 9:
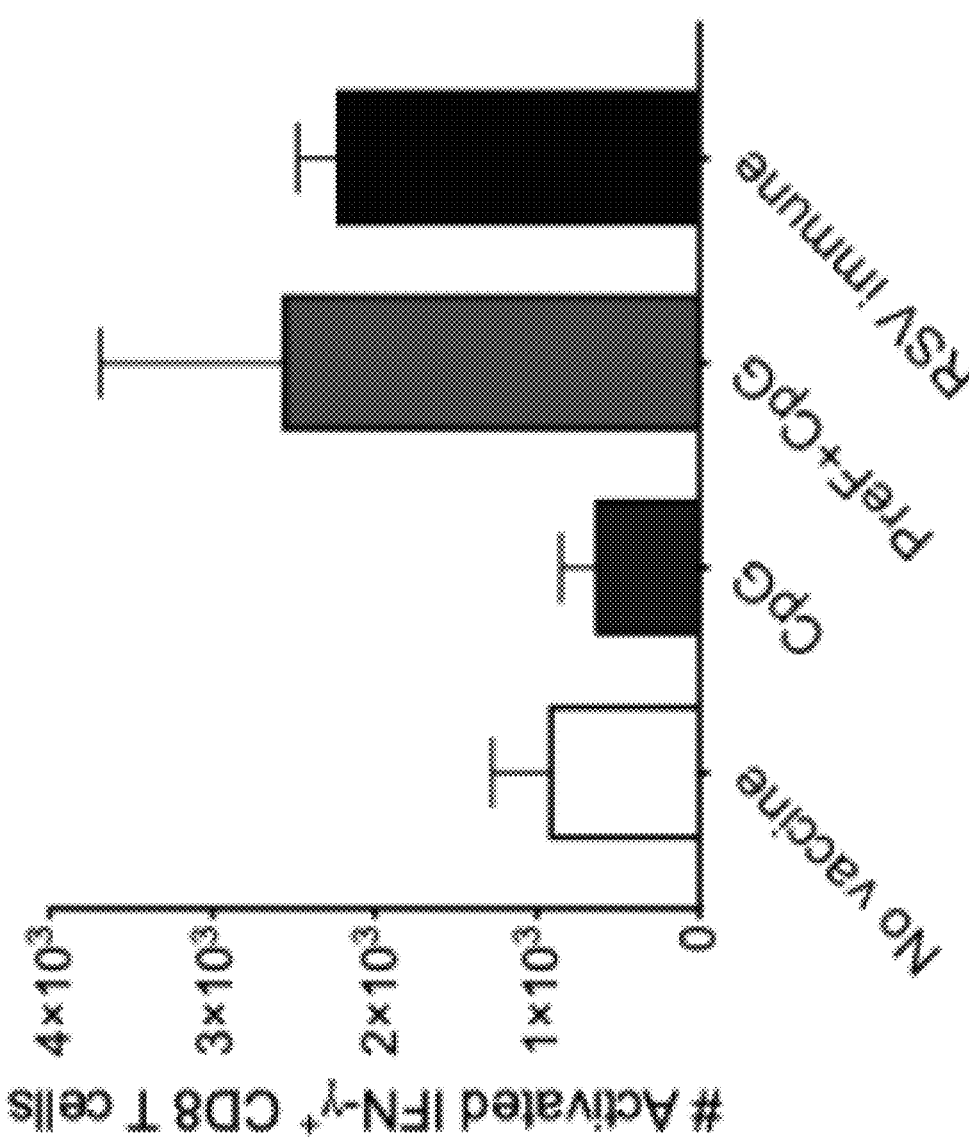
Figure 9:
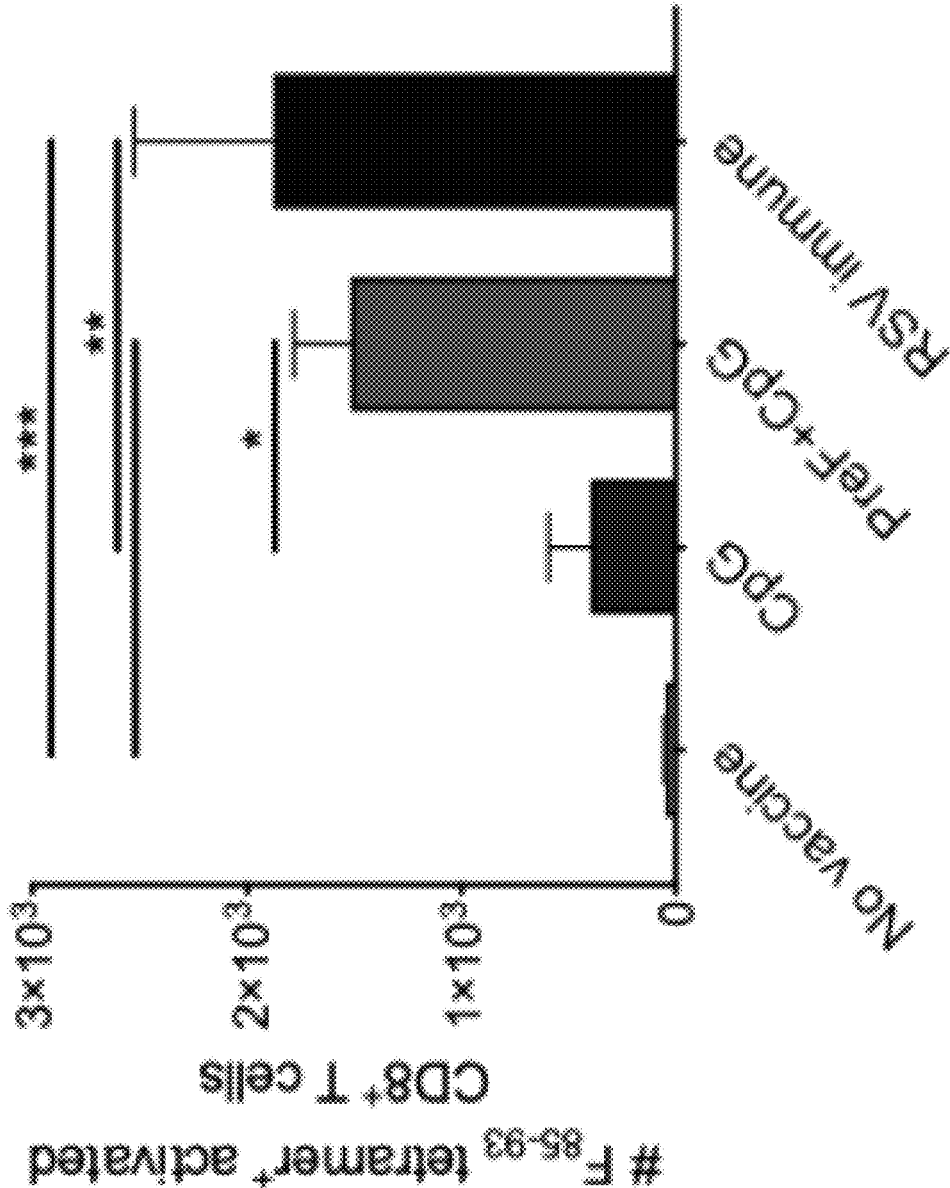
Figure 9:
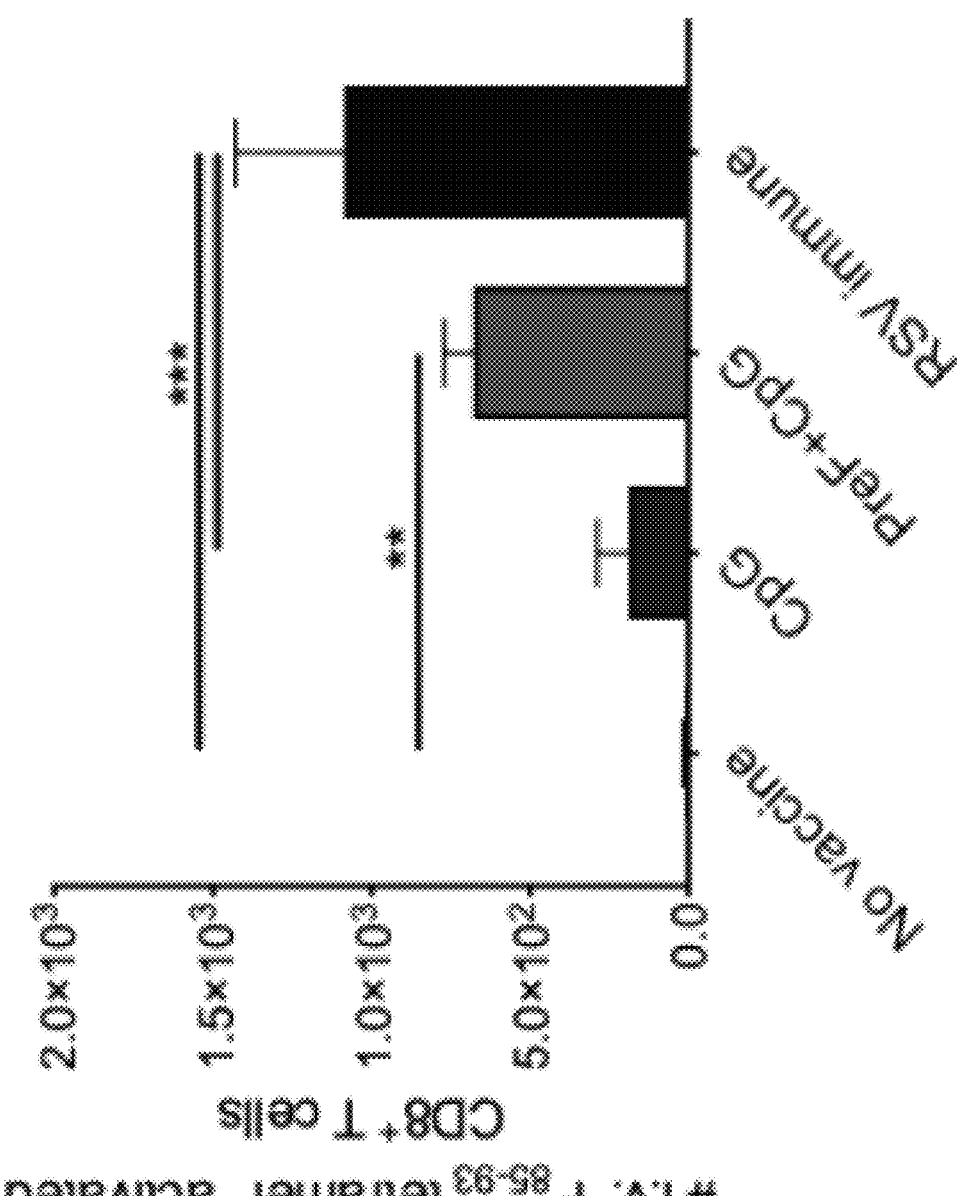

FIG. 9. Prime/boost nanoparticle vaccination with prefusion RSV F induces tissue-resident CD4 and CD8 T cells. BALB/c mice were primed with 500 µg of the indicated nanoparticle formulation i.n. on day 0, and boosted with 500 µg i.n. on day 28. No vaccine mice were administered PBS i.n. on both prime and boost days. RSV immune mice received 4.8×10$^{6}$ PFU RSV-A2 i.n. at the prime and PBS i.n. at the boost. Lungs were harvested on day 42 and analyzed by flow cytometry. Number of activated CD45 intravascular antibody (i.v.$^{-}$) (A) CD103$^{-}$CD69$^{+}$ CD4 T cells and (B) CD103$^{+}$CD69$^{+}$ CD8 T cells. Number of activated IFN-γ$^{+}$ (C) CD4 and (D) CD8 T cells following stimulation with PMA/ionomycin. Number of (E) activated F$_{85-93}$ tetramer$^{+}$ CD8 T cells and (F) i.v.$^{-}$ activated F$_{85-93}$ tetramer$^{+}$CD8 T cells. Statistical significance was determined by one-way ANOVA (C-F) with Tukey's post hoc test. *p<0.05, p<0.01, *p<0.001.

Figure 10:
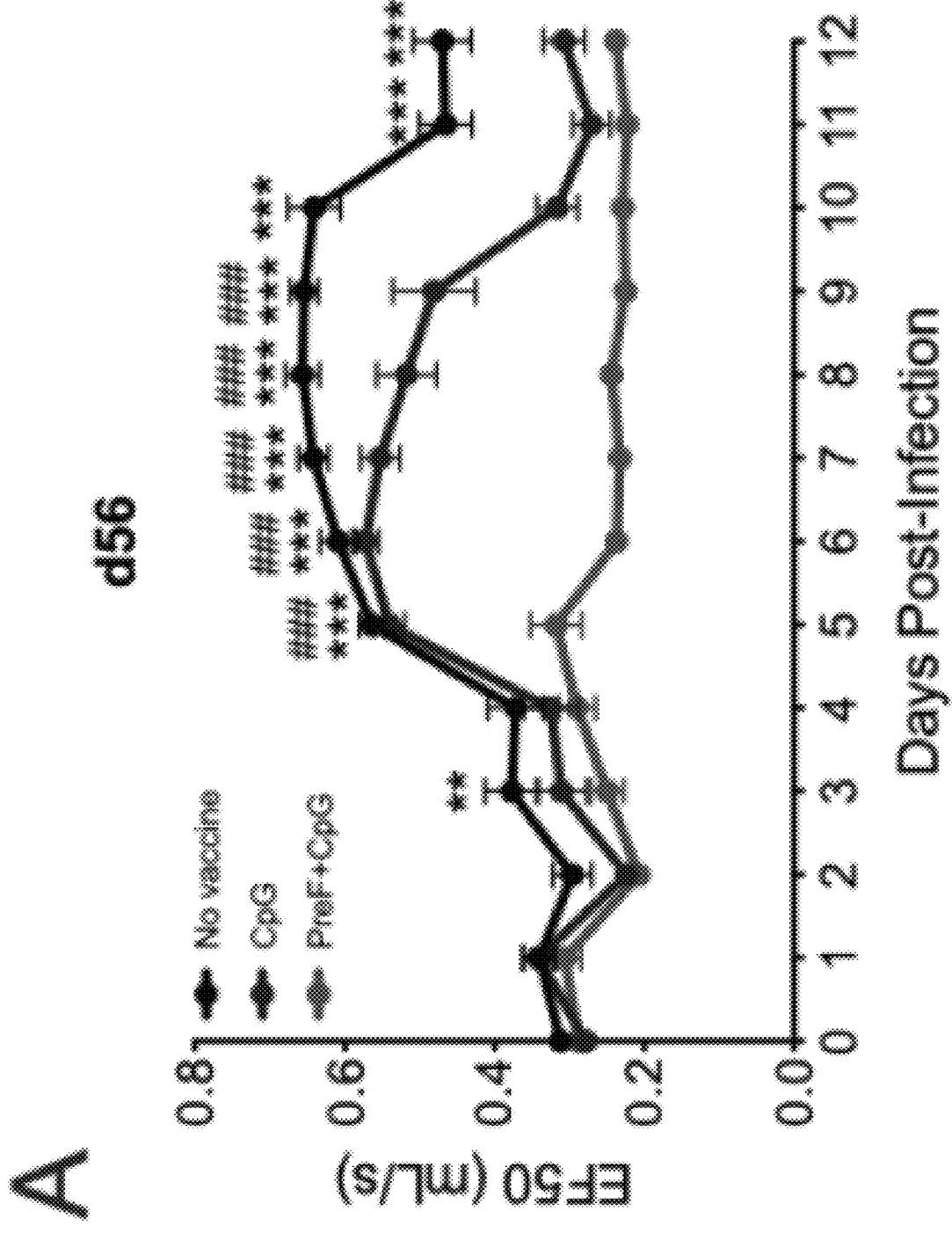
Figure 10:
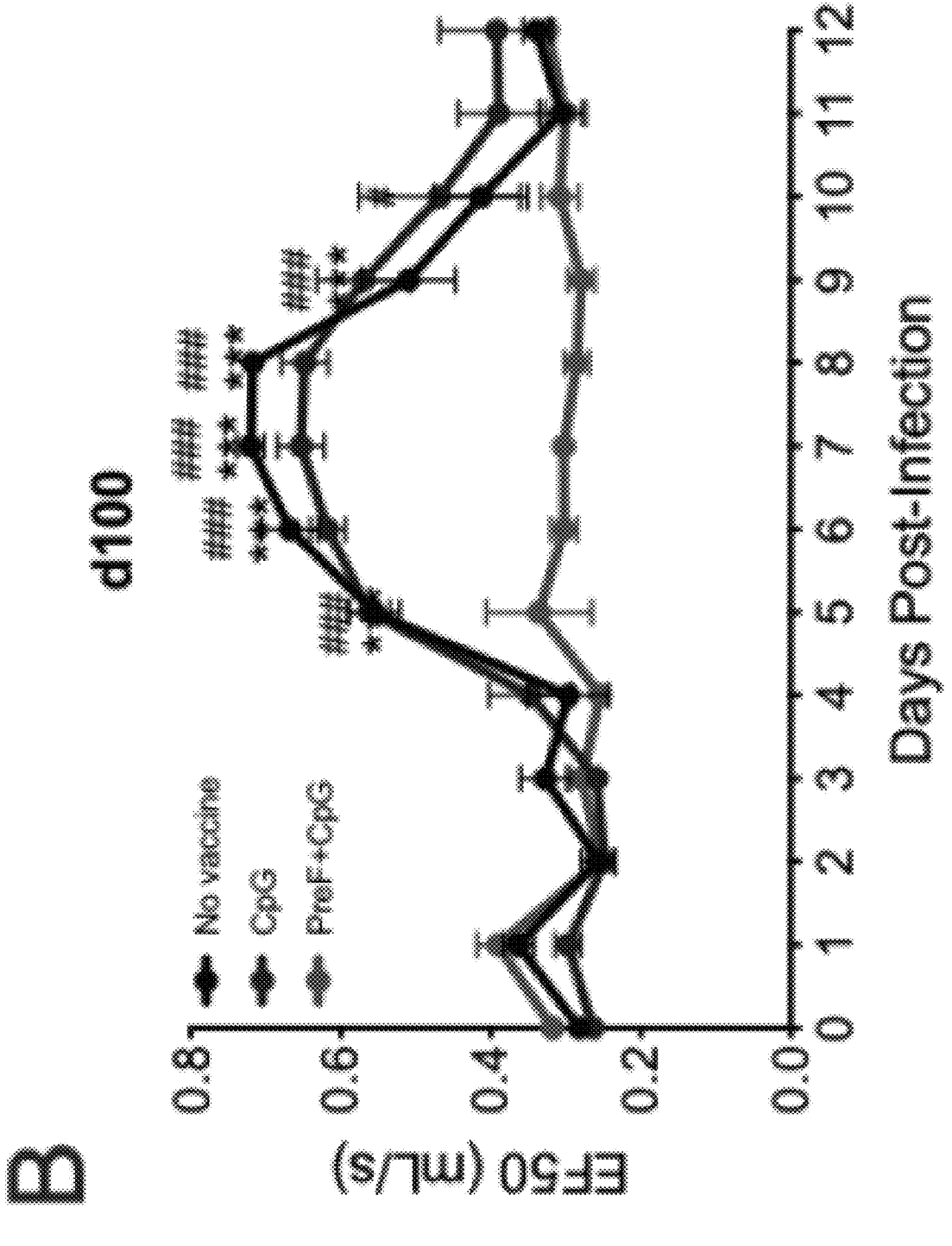
Figure 10:
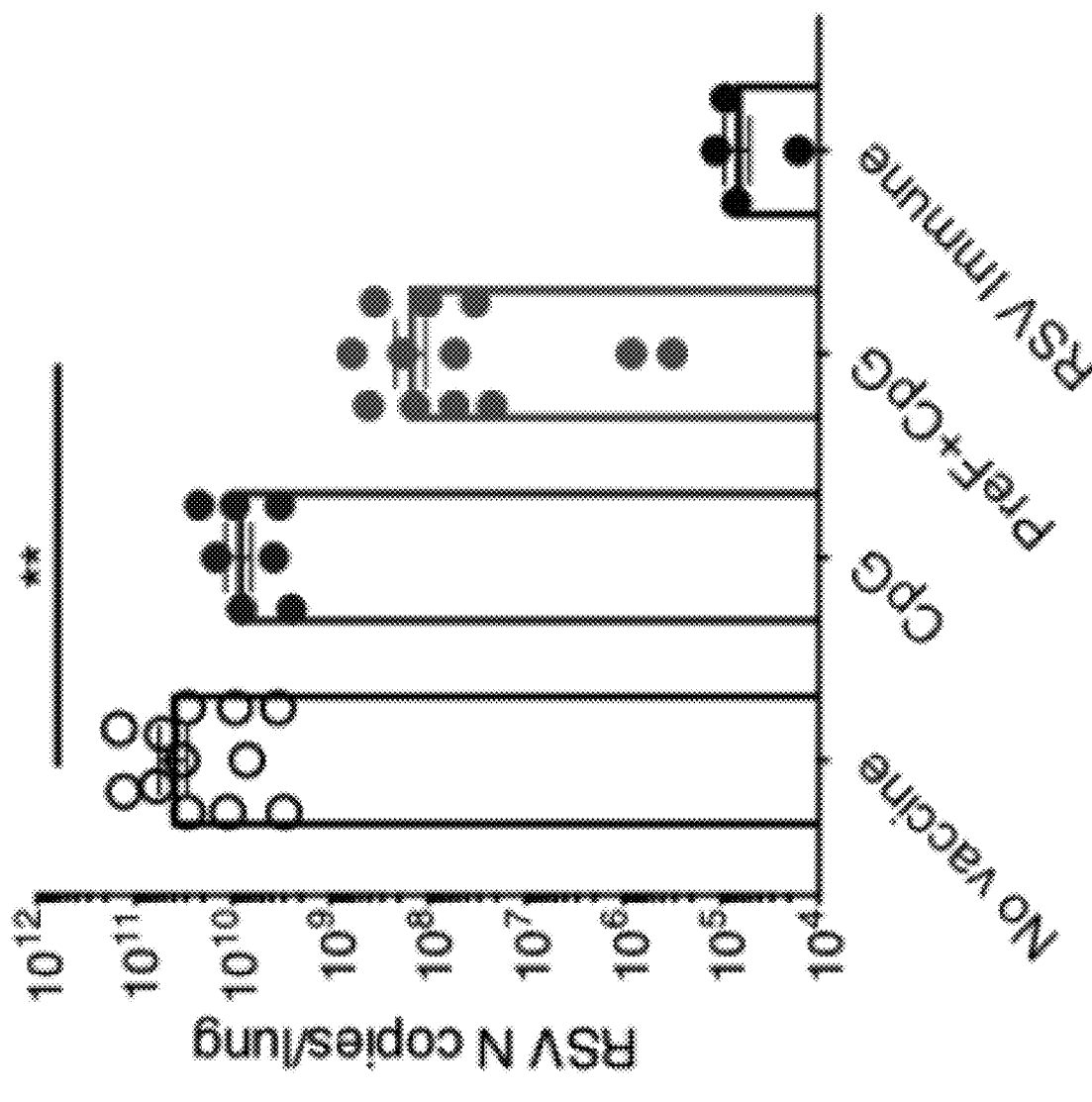

FIG. 10. BALB/c mice were primed with 500 µg of the indicated nanoparticle formulation i.n. on day 0, and boosted with 500 µg i.n. on day 28. No vaccine mice were administered PBS i.n. on both prime and boost days. RSV immune mice received 4.8×10$^{6}$ PFU RSV-A2 i.n. at the prime and PBS i.n. at the boost. (A-B) On (A) day 56 or (B) day 100, all mice were challenged with 4.8×10$^{6}$ PFU RSV-A2 i.n and monitored daily for the respiratory parameter EF50. (C) On day 56, all groups were challenged with 4.8×10$^{6}$ PFU RSV-A2 i.n and RSV N gene copy numbers per lung on day 4 were determined by RT-PCR. Asterisks represent significance between no vaccine and preF+CpG and pound symbols represent significance between CpG and preF+CpG as determined by (A-B) 2-way ANOVA or (C) one-way ANOVA with Tukey's post hoc test. *$^{/#}$p<0.05, $^{/##}$p<0.01, *$^{/###}$p<0.001.

Figure 11:
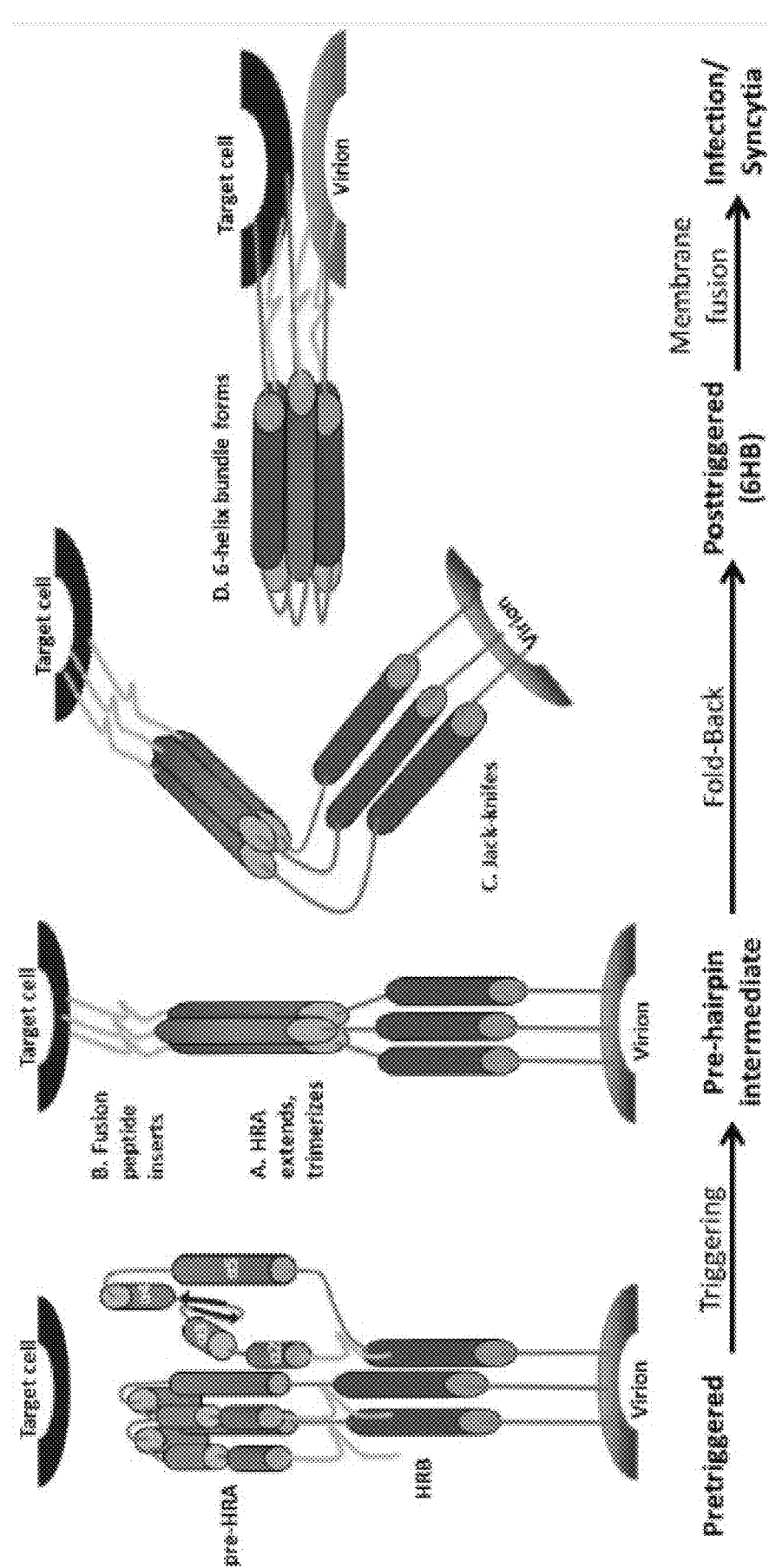

FIG. 11. Illustration of Pre-F protein triggering, fold-back, and facilitating membrane fusion between a target cell and a virion.

Figure 12:
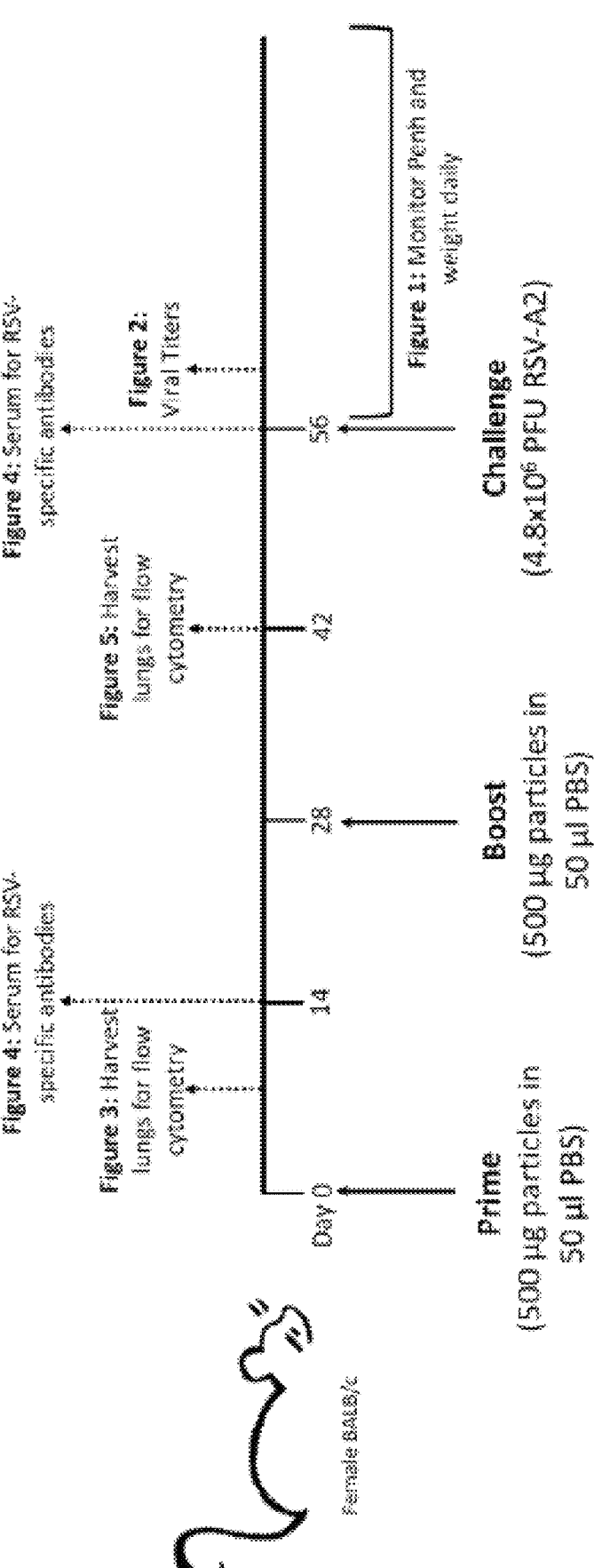

FIG. 12. Illustrative vaccination schedule.

DETAILED DESCRIPTION

The disclosed subject matter further may be described utilizing terms as defined below.

Unless otherwise specified or indicated by context, the terms "a", "an", and "the" mean "one or more." For example, "a protein" and "an adjuvant" should be interpreted to mean "one or more proteins" and "adjuvants," respectively.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

The terms "subject," "patient," and "individual" may be used interchangeably herein. A subject may be a human subject. A subject may refer to a human subject having or at risk for infection by respiratory syncytial virus (RSV). Human RSV (HRSV) is the leading cause of severe respiratory infections in neonates and children. HRSV belongs to the Orthopneumovirus genus within the Pneumoviridae family of viruses. HRSV is enveloped and has a negative-sense, single-stranded RNA genome of approximately 15 kb that encodes 11 viral proteins which include the F (fusion) protein that is a transmembrane protein of the virus and the M (matrix) protein that is a core protein of the virus. The HRSV-GNA435/11 strain has been sequenced and includes 15,277 bp encoding 11 viral proteins. (See Lee et al., Complete Genome Sequence of Human Respiratory Syncytial Virus Genotype A with a 72-Nucleotide Duplication in the Attachment Protein G Gene, J. Virol., December 2012, Vol. 86, No. 24, p. 13810-13811, the content of which is incorporated herein by reference in its entirety). The corresponding DNA sequence of the HRSV genome is provided herein as SEQ ID NO:1. The amino acid sequences of the NS1, NS2, N, M, P, G, F, SH, MS-1, MS-2, and L genes are provided herein as SEQ ID NOs: 2-12, respectively.

The disclosed compositions may include an effective amount of respiratory syncytial virus (RSV) F protein in a pre-fusion stabilized form incorporated into biodegradable polyanhydride polymer particles. The RSV F protein is a class I viral fusion glycoprotein that mediates membrane fusion between RSV and a host cell during viral entry. The F protein undergoes a conformation change from a "pre-fusion" to a "post-fusion" state during virus entry. (See FIG. 11). Some neutralizing antibodies against RSV have been shown to bind to a site called (Ø), which is present only in the pre-fusion form of F protein. Recombinant stabilized pre-fusion forms of F protein have been disclosed in the art and have been shown to be more effective at inducing neutralizing antibodies. (See Steff et al., Nat. Commun., 8:1085 (2017), pages 1-10; Blais et al., J. Virol. 91, e02437-16 (2017); McLellan et al., Science 342, 593-598 (2013); Krarup et al., Nat. Commun. 6, 8143 (2015); and Joyce et al., Nat. Struct. Mol. Biol. 23, 611-820 (2016); the contents of which are incorporated herein by reference in their entireties. Pre-fusion stabilized forms of F protein that are disclosed in the art include forms called DS-Cav1, DS-TriC, Cav-1-TriC, and DS-Cav1-TriC (see McLellan et al., Science 342, 593-598 (2013)), Pre-F-GCN4t (see Blais et al., J. Virol. 91, e02437-16 (2017)), and SC-DM, and SC-TM Krarup et al., Nat. Commun. 6, 8143 (2015)).

The disclosed compositions may include an effective amount of respiratory syncytial virus (RSV) M protein incorporated into biodegradable polyanhydride polymer particles. The M protein of RSV is a core protein that may be important for inducing a cell-mediated response against RSV infection.

Optionally, the disclosed compositions may include an effective amount of other respiratory syncytial virus (RSV) proteins incorporated into biodegradable polyanhydride polymer particles. Other proteins or RSV may include one or more of the RSV proteins selected from NS1, NS2, N, P, SH, G, M2-1, M2-2, L, or any combinations thereof.

As used herein, the phrase "effective amount" shall mean that dosage that provides the specific immunological response for which a composition comprising that effective amount is administered in a significant number of subjects. For example, an effective amount of an antigen may include that amount which when administered to a vaccinee induces an immune response in the vaccinee, preferably a protective immune response against the pathogen from which the antigen is derived. An effective amount of an antigen that is administered to a particular patient in a particular instance will not always be effective in treating the conditions/diseases described herein, even though such dosage is deemed to be a therapeutically effective amount by those of skill in the art.

The compositions disclosed herein may be formulated as vaccine compositions for administration to a subject in need thereof. Such compositions can be formulated and/or administered in dosages and by techniques well known to those skilled in the medical arts taking into consideration such factors as the age, sex, weight, and condition of the particular patient, and the route of administration.

The compositions may include pharmaceutical solutions comprising carriers, diluents, excipients, and surfactants as known in the art. Further, the compositions may include preservatives. The compositions also may include buffering agents.

The disclosed compositions typically include biodegradable particles. The biodegradable particles typically have an average effective diameter of less than about 5, 4, 3, 2, 1, 0.5, 0.1, 0.05, or 0.01 μM, or the biodegradable particles have an average effective diameter within a range bounded by any of these values (e.g., 0.1-2 μM).

In some embodiments, the disclosed particles may be phagocytosed by antigen presenting cells, such as macrophage and dendritic cells, when the disclosed particles are administered as an immunogenic composition or vaccine formulation to a subject in need thereof. Preferably, the disclosed particles have an effective average diameter to permit phagocytosis by antigen presenting cells. Particles larger than about 5 microns are unlikely to be phagocytosed by antigen presenting cells and preferably the particles have an effective average diameter of less than about 4 microns or more preferably the particles have an effective average diameter of less than about 3 microns.

The disclosed particles typically are biodegradable as would be understood in the art. The term "biodegradable" describes a material that is capable of being degraded in a physiological environment into smaller basic components by biochemical reactions and/or physical reactions. The term "biodegradable" may be used herein interchangeably with the term "bioerodible." Preferably, the biodegradable particles are degraded (or eroded) into smaller basic components are innocuous. For example, a biodegradable polymer may be degraded into basic components that include, but are not limited to, water, carbon dioxide, sugars, organic acids (e.g., tricarboxylic or amino acids), and alcohols (e.g., glycerol or polyethylene glycol).

The disclosed compositions typically include biodegradable polyanhydride polymer particles which may include particles comprising or formed from homopolymers or copolymers. Biodegradable polyanhydride homopolymer and copolymer particles are known in the art. (See, e.g., U.S. Pat. Nos. 8,173,104 and 7,858,093, the contents of which are incorporated herein by reference in their entireties). In some embodiments, the biodegradable polyanhydride polymer particles comprise a polymer formed from a 1,ω-bis(p carboxyphenoxy)(C$_2$-C$_{12}$)alkane, a 1,ω-bis(p-carboxyphenoxy)(C$_2$-C$_{12}$)dioxa-alkane, and a (C$_5$-C$_{20}$)alkanoic diacid. In particular, the biodegradable polyanhydride polymer particles may comprise a polymer formed from 1,6-bis(p-carboxyphenoxy)hexane (CPH), 1,8-bis(p-carboxyphenoxy)-3,6-dioxaoctane (CPTEG), and sebacic acid (SA). Where the biodegradable polyanhydride polymer particles are comprised of a polymer formed from CPH and CPTEG, the ratio of CPH and CPTEG may be modulated to prepare particles having a suitable release profile. In some embodiments, the biodegradable polyanhydride polymer particles comprise a polymer formed from CPH and CPTEG at a ratio CPH:CPTEG selected from 10:90, 20:80, 30:70, 40:60, 50:50, 60:40, 70:30, 80:20, and 90:10, or within a range bounded by any of these ratios (e.g., 80-60:20-40 CPH: CPTEG). In some embodiments, the biodegradable polyanhydride polymer particles may be formulated to enhance uptake by and activation of dendritic cells. (See Carrillo-Conde et al., Acta Biomaterialia 8 (2012) 3618-3628; the content of which is incorporated herein by reference in its entirety)

Other biodegradable materials that may be utilized to prepare the particles contemplated herein may include materials disclosed in one or more of U.S. Pat. Nos. 7,470,283; 7,390,333; 7,128,755; 7,094,260; 6,830,747; 6,709,452; 6,699,272; 6,527,801; 5,980,551; 5,788,979; 5,766,710; 5,670,161; and 5,443,458; and U.S. Published Application Nos. 20090319041; 20090299465; 20090232863; 20090192588; 20090182415; 20090182404; 20090171455; 20090149568; 20090117039; 20090110713; 20090105352; 20090082853; 20090081270; 20090004243; 20080249633; 20080243240; 20080233169; 20080233168; 20080220048; 20080154351; 20080152690; 20080119927; 20080103583; 20080091262; 20080071357; 20080069858; 20080051880; 20080008735; 20070298066; 20070288088; 20070287987; 20070281117; 20070275033; 20070264307; 20070237803; 20070224247; 20070224244; 20070224234; 20070219626; 20070203564; 20070196423; 20070141100; 20070129793; 20070129790; 20070123973; 20070106371; 20070050018; 20070043434; 20070043433; 20070014831; 20070005130; 20060287710; 20060286138; 20060264531; 20060198868; 20060193892; 20060147491; 20060051394; 20060018940; 20060009839; 20060002979; 20050283224; 20050278015; 20050267565; 20050232971; 20050177246; 20050169968; 20050019404; 20050010280; 20040260386; 20040230316; 20030153972; 20030153971; 20030144730; 20030118692; 20030109647; 20030105518; 20030105245; 20030097173; 20030045924; 20030027940; 20020183830; 20020143388; 20020082610; and 0020019661; the contents of which are incorporated herein by reference in their entireties.

Typically, the biodegradable particles disclosed herein are degraded in vivo at a degradation rate such that the particles lose no more than about 20%, 30%, 40%, 50%, 60%, 70%, 80%, 90%, 95%, or 99% of their initial mass (or within a range bounded by any of these values) after about 1, 2, 3, 4, 5, 6, 7, or 8 weeks or more post-administration (or within a range bounded by any of these values). The particles may comprise or may be formed from polymeric or non-polymeric biodegradable material. If the particles comprise polymeric material, typically the particles are degraded into biodegradable monomers. If the particles comprise non-polymeric material, typically the particles are degraded into biodegradable components.

The disclosed biodegradable particles may be prepared by methods known in the art including, but not limited to, spray-drying, precipitation, and grinding. In some embodiments, the biodegradable particles may be formed from a solution or suspension of a biodegradable material optionally in the presence of one or more additional agents such as adjuvants, apoptosis inhibitors, and/or antigens (e.g., by spray-drying the solution or suspension). As such, the biodegradable particles may comprise biodegradable material and optionally may comprise one or more additional agents such as adjuvants, apoptosis inhibitors, and/or antigens.

The disclosed biodegradable particles may be administered by various routes in order to induce a response in a subject. Routes of administration may include, but are not limited to, intranasal, pulmonary, oral, subcutaneous, intramuscular, and intravenous.

In some embodiments, the disclosed methods comprise administering a composition comprising biodegradable particles to induce an immune response in the subject. In other embodiments, the disclosed methods consist of administering a composition consisting of biodegradable particles to induce an immune response in the subject. The induced immune response may include an antibody response, a Th1 cell response and a CD8 CTL response.

The compositions disclosed herein optionally include an adjuvant. The term "adjuvant" refers to a compound or mixture that enhances an immune response. An adjuvant can serve as a tissue depot that slowly releases the antigen and also as a lymphoid system activator that non-specifically enhances the immune response. Examples of adjuvants which may be utilized in the disclosed compositions include but are not limited to, co-polymer adjuvants (e.g., Pluronic L121® brand poloxamer 401, CRL1005, or a low molecular weight co-polymer adjuvant such as Polygen® adjuvant), poly (I:C), R-848 (a Th1-like adjuvant), resiquimod, imiquimod, PAM3CYS, aluminum phosphates (e.g., AlPO$_4$), loxoribine, potentially useful human adjuvants such as BCG (Bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin (e.g., Quil-A), mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

The compositions disclosed herein may include pharmaceutical compositions that are administered as vaccines. Typically, the pharmaceutical composition comprises an effective amount or concentration of an antigen for inducing a protective or therapeutic immune response against a disease, which may include, but is not limited to infection by a pathogen such as RSV. Inducing a protective or therapeutic immune response may include inducing an antibody response, as well as a CD4 and/or CD8 T cell immune response to one or more epitopes of a protein associated with a pathogen (e.g., a protein associated with RSV). Inducing a protective or therapeutic immune response may include inducing an antibody response, as well as a Th1 response and/or a CD8 T cell response to one or more epitopes of a protein associated with the pathogen. As utilized herein, a Th1-response may be characterized by cytokine production such as interferons (e.g., IFN-γ), tumor necrosis factor (e.g., TNF), and interleukins (e.g., IL-2). A Th1-response also may be characterized by increased killing efficiency of macrophages with respect to a pathogen and the proliferation of cytotoxic CD8$^+$ cells against the pathogen. A Th1 response also may be characterized by the presence of opsonizing antibodies against the antigen.

Inducing a protective response may include inducing immunity against the pathogen, and in some embodiments, inducing protective immunity and/or sterilizing immunity against the pathogen. Inducing a therapeutic response may include reducing the pathogenic load of a subject, for example, as determined by measuring the amount of circulating pathogen before and after administering the composition. Inducing a therapeutic response may include reducing the degree or severity of at least one symptom of infection by the pathogen.

The presently disclosed methods may be utilized for inducing a protective or therapeutic immune response against disease by administering the pharmaceutical compositions disclosed herein (e.g., as immunogenic compositions or vaccines) to a subject in need thereof, which may include a human or non-human having or at risk for acquiring the disease. The methods may include administering a first pharmaceutical composition and optionally may include administering a second pharmaceutical composition to augment or boost an immunogenic response induced by the first pharmaceutical composition. The first and second pharmaceutical compositions may be the same or different. The optionally administered second pharmaceutical composition may be administered prior to, concurrently with, or after administering the first pharmaceutical composition. In some embodiments, the first composition is administered and then the second composition is administered after waiting at least about 1, 2, 3, 4, 5, or 6 weeks. The first composition (and the second composition) may be administered one or more times.

The presently disclosed compositions, kits, and methods may be utilized to protect against or treat infection by a pathogen. As used herein, a "pathogen" includes, but is not limited to a living microorganism such as bacteria, viruses, and fungi that cause disease in a host. As used herein, a "pathogen" includes respiratory syncytial virus (RSV).

The presently disclosed composition may be administered to potentiate or enhance an immune response. As used herein, "potentiating" or "enhancing" an immune response means increasing the magnitude and/or the breadth of the immune response. For example, the number of cells that recognize a particular epitope may be increased ("magnitude") and/or the numbers of epitopes that are recognized may be increased ("breadth"). Preferably, an enhanced antibody response as well as an enhancement in CD4 and/or CD8 T-cell responses may be obtained by administering the pharmaceutical composition disclosed herein.

Illustrative Embodiments

The following Embodiments are illustrative and should not be interpreted to limit the scope of the claimed subject matter.

Embodiment 1. A vaccine composition comprising an effective amount of respiratory syncytial virus (RSV) F protein in a pre-fusion stabilized form and/or M protein incorporated into biodegradable polyanhydride polymer particles for inducing an immune response against RSV.

Embodiment 2. The vaccine composition of embodiment 1, comprising an effective amount of RSV F protein in the pre-fusion stabilized form incorporated into the biodegradable polyanhydride polymer particles for inducing an immune response against RSV.

Embodiment 3. The vaccine composition of embodiment 1 or 2, wherein the F protein in a pre-fusion stabilized form is selected from the group consisting of DS-Cav1, DS-TriC, Vav-1-TriC, DX-Cav1-TriC, Pre-F-GCN4t, SC-DM, and SC-TM.

Embodiment 4. The vaccine composition of any of the foregoing embodiments, wherein the F protein in a pre-fusion stabilized form is DS-Cav1.

Embodiment 5. The vaccine composition of embodiment 1, comprising an effective amount of RSV M protein incorporated into the biodegradable polyanhydride polymer particles for inducing an immune response against RSV.

Embodiment 6 The vaccine composition of any of the foregoing embodiments, further comprising an adjuvant, optionally wherein the adjuvant is incorporated into the biodegradable polyanhydride polymer particles.

Embodiment 7. The vaccine composition of any of the foregoing embodiments, further comprising a CpG oligonucleotide, optionally wherein the CpG oligonucleotide is incorporated into the biodegradable polyanhydride polymer particles.

Embodiment 8. The vaccine composition of any of the foregoing embodiments, further comprising a CpG oligodeoxynucleotide (ODN), optionally wherein the CpG ODN is incorporated into the biodegradable polyanhydride polymer particles.

Embodiment 9. The vaccine composition of any of the foregoing embodiments, wherein the particles have an average effective diameter of less than about 5, 4, 3, 2, 1, 0.5, 0.1, 0.05, or 0.01 μM, or have an average effective diameter within a range bounded by any of these values (e.g., 2-0.1 μM).

Embodiment 10. The vaccine composition of any of the foregoing embodiments, wherein the vaccine composition induces an antibody response as well as a CD4 T cell response (e.g., a Th1-type response), a CD8 T cell response, or a combination thereof.

Embodiment 11. The vaccine composition of any of the foregoing embodiments, wherein biodegradable polyanhydride polymer particles comprise a polymer formed from a 1,ω-bis(p-carboxyphenoxy)($C_2$-$C_{12}$)alkane, a 1,ω-bis(p-carboxyphenoxy)($C_2$-$C_{12}$)dioxa-alkane, and a ($C_5$-$C_{20}$)alkanoic diacid.

Embodiment 12. The vaccine composition of any of the foregoing embodiments, wherein the biodegradable polyanhydride polymer particles comprise a polymer formed from 1,6-bis(p-carboxyphenoxy)hexane (CPH), 1,8-bis(p-carboxyphenoxy)-3,6-dioxaoctane (CPTEG), and sebacic acid (SA).

Embodiment 13. The vaccine composition of any of the foregoing embodiments, wherein the biodegradable polyanhydride polymer particles comprise a polymer formed from 1,6-bis(p-carboxyphenoxy)hexane (CPH), 1,8-bis(p-carboxyphenoxy)-3,6-dioxaoctane (CPTEG), and sebacic acid (SA), wherein the polymer is formed from CPH and CPTEG at a ratio CPH:CPTEG selected from 10:90, 20:80, 30:70, 40:60, 50:50, 60:40, 70:30, 80:20, and 90:10, or within a range bounded by any of these ratios (e.g., 80-60:20-40 CPH:CPTEG).

Embodiment 14. The vaccine composition of any of the foregoing embodiments, wherein the biodegradable polyanhydride polymer particles comprise a polymer formed from 1,6-bis(p-carboxyphenoxy)hexane (CPH), 1,8-bis(p-carboxyphenoxy)-3,6-dioxaoctane (CPTEG), and sebacic acid (SA), wherein the polymer is formed from CPH and CPTEG at a ratio CPH:CPTEG of about 80:20.

Embodiment 15. The vaccine composition of any of the foregoing embodiments, further comprising an RSV protein selected from NS1, NS2, N, P, SH, G, M2-1, M2-2, L, or any combinations thereof.

Embodiment 16. A method comprising administering any of the foregoing vaccine compositions to a subject who is at risk for infection by RSV.

Embodiment 17. The method of embodiment 16, wherein after the vaccine composition is administered to the subject, the subject is protected against infection by RSV.

Embodiment 18. The method of embodiment 16 or 17, wherein the vaccine composition is administered by a route selected from intranasal, pulmonary, oral, subcutaneous, intramuscular, or intravenous.

EXAMPLES

The following Examples are illustrative and should not be interpreted to limit the scope of the claimed subject matter.

Title—Evaluation of a Polyanhydride-Based Nanoparticle Vaccine Utilizing RSV M and/or Profusion F Reference is made to the poster presentation entitled "Evaluation of a polyanhydride-based nanoparticle vaccine utilizing RSV M and/or prefusion F," presented at the $11^{th}$ International Respiratory Syncytial Virus Symposium, Oct. 31-Nov. 4, 2018, which is incorporated herein by reference in its entirety.

Abstract

Respiratory syncytial virus (RSV) is the leading cause of lower respiratory tract infections in young children, resulting in 34 million new RSV infections each year, and approximately 125,000 hospitalizations annually in the United States alone. RSV reinfection is common in children, and even adults can be susceptible to repeated infection due to short-lived and incomplete protective immunity following natural infection. Despite the critical need, there is currently no licensed vaccine for RSV. Here we developed a polyanhydride nanoparticle-based vaccine utilizing the RSV matrix (M) protein and/or a prefusion-stabilized variant of the RSV fusion (F) protein (DS-Cav1). Our nanoparticle formulation offers several advantages over current vaccine strategies as it allows for continual, controlled release of the antigen and has been shown to induce robust T and B cell responses when paired with antigens from other pathogens. Inclusion of the prefusion conformation of RSV F within the vaccine allows for better exposure of the major RSV F antigenic site, termed site Ø, while the RSV M protein contains epitopes that are known targets of both CD4 and CD8 T cell responses. The RSV nanovaccine is composed of 20:80 1,8-bis(p-carboxyphenoxy)-3,6-dioxoctane (CPTEG):1,6-bis(p-carboxyphenoxy)hexane (CPH) copolymer nanoparticles encapsulating the M and DS-Cav1 prefusion F proteins with CpG 1668 ODN. Additional formulations include RSV F in its postfusion conformation with CpG, and DS-Cav1 protein and CpG. Controls consist of nanoparticles containing either pre-F or postfusion RSV F without CpG, and nanoparticles loaded with CpG alone. Here we evaluated the immunogenicity and the protective capacity of our nanoparticle vaccine strategy against a primary RSV infection.

Methods

BALB/c mice were vaccinated intranasally with 500 μg of the nanoparticles in PBS administered at day 0 and subsequently boosted intranasally at day 28. (See FIG. 12). At day 56 the protective capacity of the nanoparticles was assessed by determining viral titers in the lungs of vaccinated mice following an RSV challenge. Using whole body plethysmography, we also measured airway function to determine the capacity of the RSV nanovaccine to protect against RSV-induced pulmonary injury. Lungs were harvested post-prime or post-boost to evaluate the T and B cell responses elicited by the nanoparticle vaccination.

Results

The inventors are using the M+prefusion RSV F nanoparticle vaccine to determine the optimal vaccine regimen to provide protection against RSV-induced disease. Additionally, the inventors are investigating the ideal mixture of humoral and cell-mediated immunity necessary to establish long-term protective immunity against RSV. Information from these studies will be critical to establish optimal thresholds for protective immunity against RSV.

Figure 1:
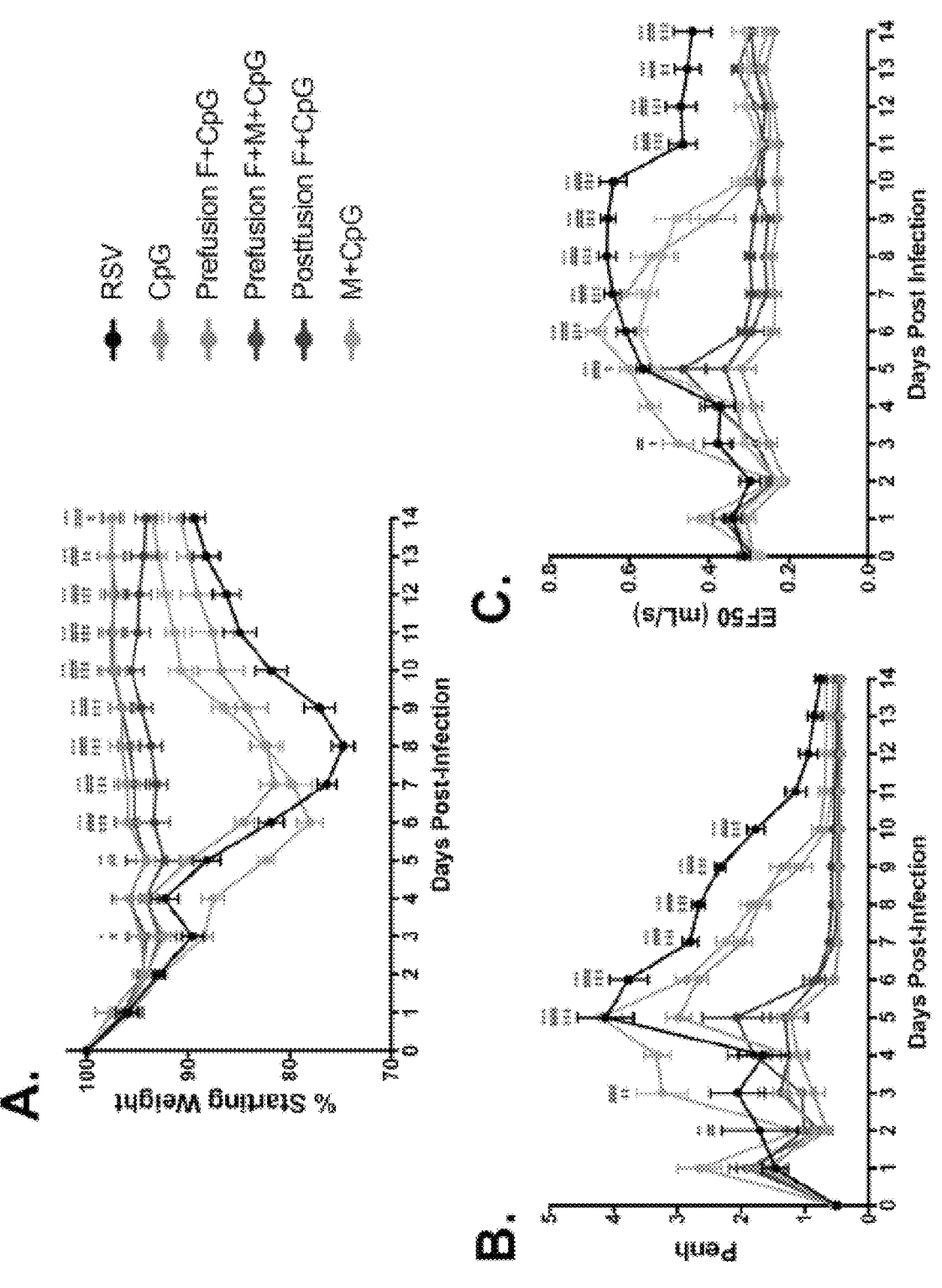
FIG. 1. Prime/boost nanoparticle vaccination strategy with prefusion RSV F protects against RSV-induced disease. BALB/c mice were primed with 500 μg of the indicated nanoparticle formulation i.n. on day 0, and boosted with 500 μg i.n. on day 28. Control mice (labeled RSV) were administered PBS i.n. on both prime and boost days. On day 56, all mice were challenged with $4.8 \times 10^6$ PFU RSV-A2 i.n. and assessed for (A) weight loss, (B) Penh, and (C) EF50. Data are represented as mean±SEM of 3 independent experiments (n=11 mice for prefusionF+M+CpG, n=12 mice for RSV, CpG, M+CpG, and postfusion F+CpG, n=10 mice for prefusion F+CpG). Asterisks represent significance between RSV and prefusion F+M+CpG, pound symbols represent significance between RSV and prefusion F+CpG, and ‡ represents significance between RSV and postfusion F+CpG as determined by a 2-way ANOVA with a Dunnett's post hoc test. $^{*/\#/\ddagger}p<0.05$, $^{/\#\#/\ddagger\ddagger}p<0.01$, $^{*/\#\#\#/\ddagger\ddagger\ddagger}p<0.001$ FIG. 2. Prime/boost nanoparticle vaccination with prefusion RSV F reduces RSV N gene viral copy numbers. BALB/c mice were primed with 500 μg of the indicated nanoparticle formulation i.n. on day 0, and boosted with 500 μg i.n. on day 28. Control mice (labeled RSV) were administered PBS i.n. on both prime and boost days. On day 56, all mice were challenged with $4.8 \times 10^6$ PFU RSV-A2 i.n. 4 days post-challenge lungs were harvested for RNA. RT-PCR was performed to determine RSV N gene copy numbers. Data represent mean±SEM of 2 independent experiments (n=8 mice for postfusion F+CpG, M+CpG, and prefusion F+CpG, n=7 mice for RSV, n=6 mice for prefusion F+M+CpG, n=4 mice for CpG). Statistical significance was determined by a one-way ANOVA with a Tukey's post hoc test. $^*p<0.05$, $^{**}p<0.01$ FIG. 3. Initial priming vaccination with prefusion RSV F induces lung-resident CD4 and CD8 T cells. BALB/c mice were primed with 500 μg of the indicated nanoparticle formulation or PBS (naïve) i.n. on day 0. Lungs and spleen were harvested on day 8 and analyzed by flow cytometry. Frequency of (A) activated ($CD11a^{hi}CD49^+$) CD4 T cells and (B) activated ($CD11a^{hi}CD8^{lo}$) CD8 T cells. Number of i.v.⁻ (C) CD4 and (D) CD8 T cells. Number of activated i.v⁻ (E) $CD103^-CD69^+$ CD4 T cells and (F) $CD103^+CD69^+$ CD8 T cells. (G) Representative flow cytometry plots of germinal center B cells ($CD19^+CDB220^+Fas^+GL-7^+$). Data are represented as mean±SEM from a single experiment (n=4 mice for naïve, preF+CpG, preF+M+CpG, n=3 mice for CpG, PreF, PreF+M). Statistical significance was determined by a 2-way ANOVA with Tukey's post hoc test (A and B). $^*p<0.05$, $^{}p<0.01$, $^{*}p<0.001$ FIG. 4. Prime/boost nanoparticle vaccination induces RSV-specific antibodies in serum. BALB/c mice were primed with 500 μg of the indicated nanoparticle formulation i.n. on day 0, and boosted with 500 μg i.n. on day 28. Control mice (labeled naïve) were administered PBS i.n. on both prime and boost days. On day 14 and 56 serum was assessed for (A,D) total RSV-specific IgG, (B,E) IgG1, or (C,F) IgG2a. Data are represented as mean±SEM from a single experiment (n=4 mice). Asterisks represent significance between naive and prefusion F+M+CpG, and ‡ represents significance between naive and postfusion F+CpG as determined by a 2-way ANOVA with Dunnett's post hoc test. *$^{/#/‡}$p<0.05, $^{/##/‡‡}$p<0.01, *$^{/###/‡‡‡}$p<0.001.

The results in FIG. 1 illustrate that a prime/boost nanoparticle vaccination strategy with prefusion RSV F protects against RSV-induced disease. BALB/c mice were primed with 500 μg of the indicated nanoparticle formulation i.n. on day 0, and boosted with 500 μg i.n. on day 28. Control mice (labeled RSV) were administered PBS i.n. on both prime and boost days. On day 56, all mice were challenged with $4.8\times10^6$ PFU RSV-A2 i.n. and assessed for weight loss, Penh, and EF50.

Figure 2:
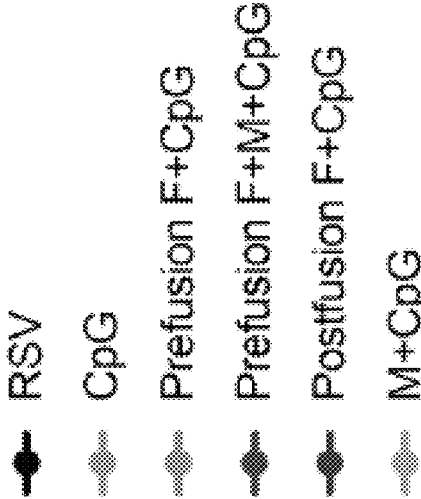
Figure 2:
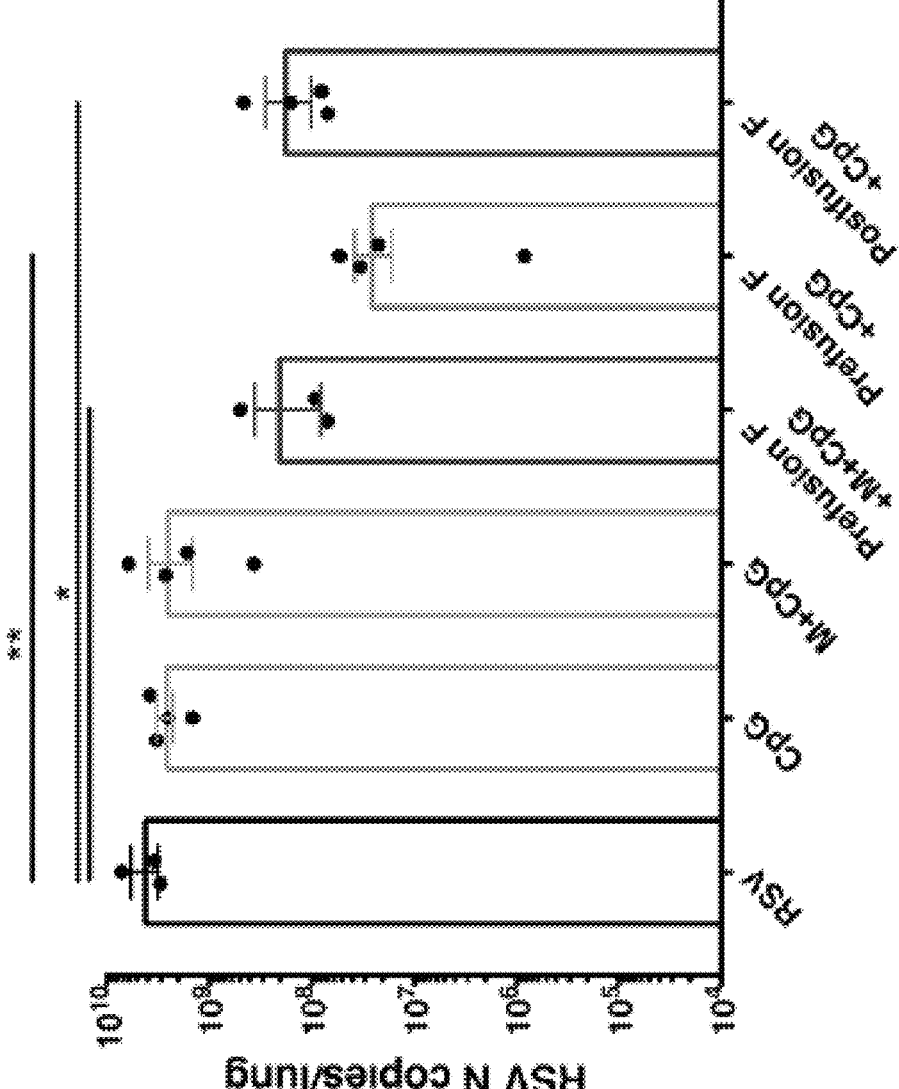

FIG. 2 illustrates that prime/boost nanoparticle vaccination with prefusion RSV F reduces RSV N gene viral copy numbers. BALB/c mice were primed with 500 μg of the indicated nanoparticle formulation i.n. on day 0, and boosted with 500 μg i.n. on day 28. Control mice (labeled RSV) were administered PBS i.n. on both prime and boost days. On day 56, all mice were challenged with $4.8\times10^6$ PFU RSV-A2 i.n. 4 days post-challenge lungs were harvested for RNA. RT-PCR was performed to determine RSV N gene copy numbers.

Figure 3:
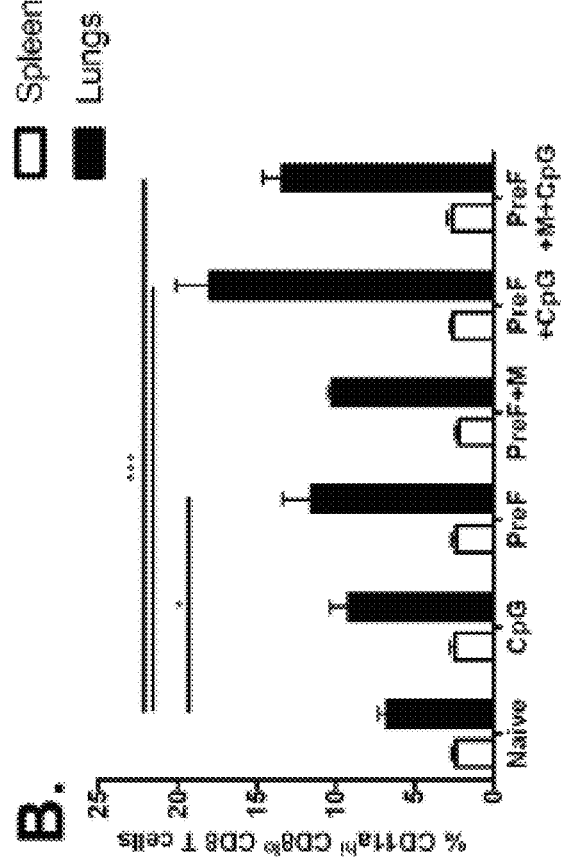
Figure 3:
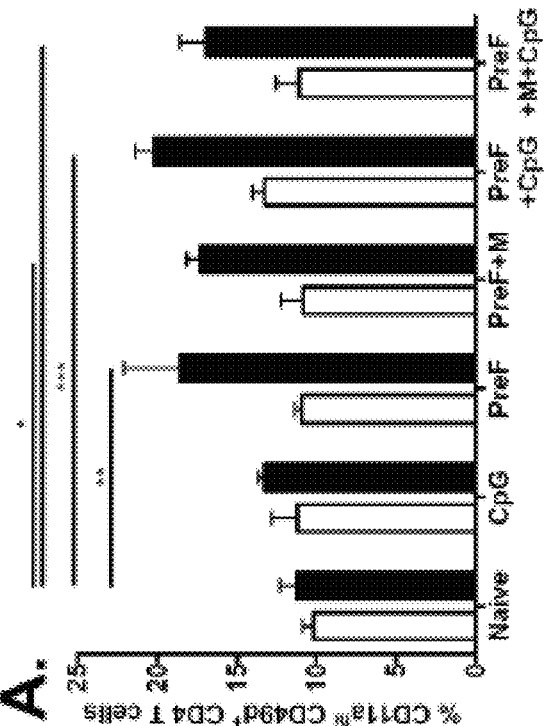
Figure 3:
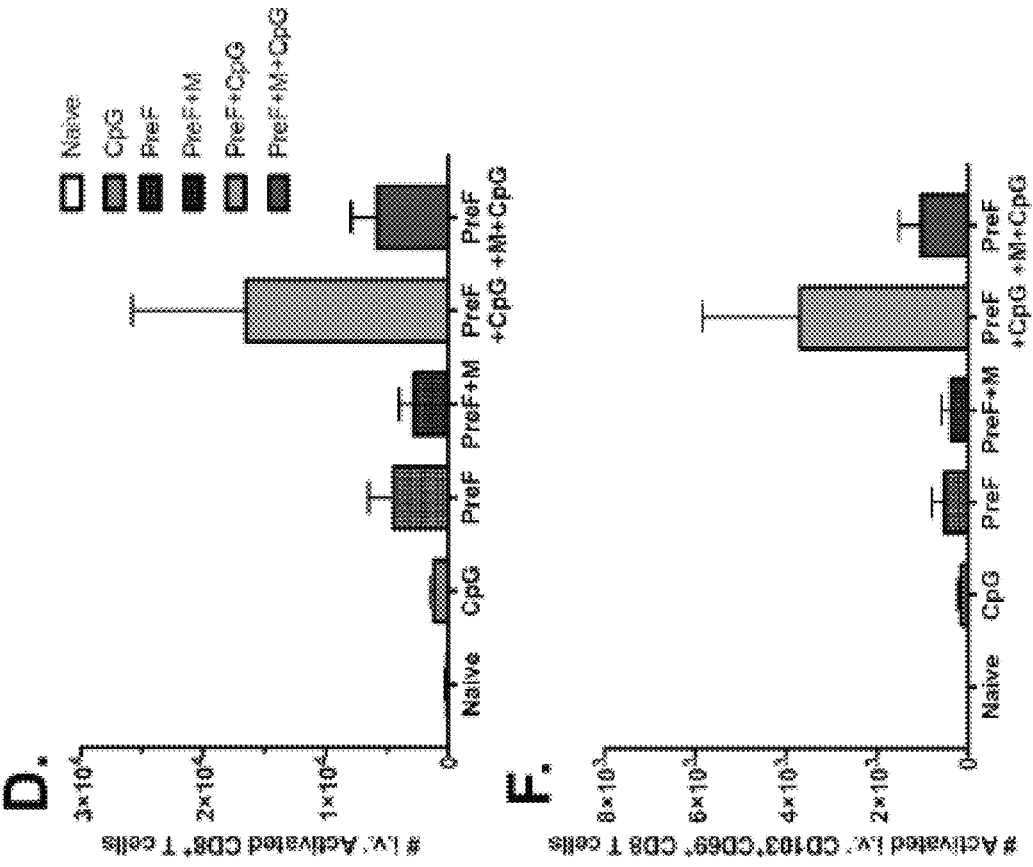
Figure 3:
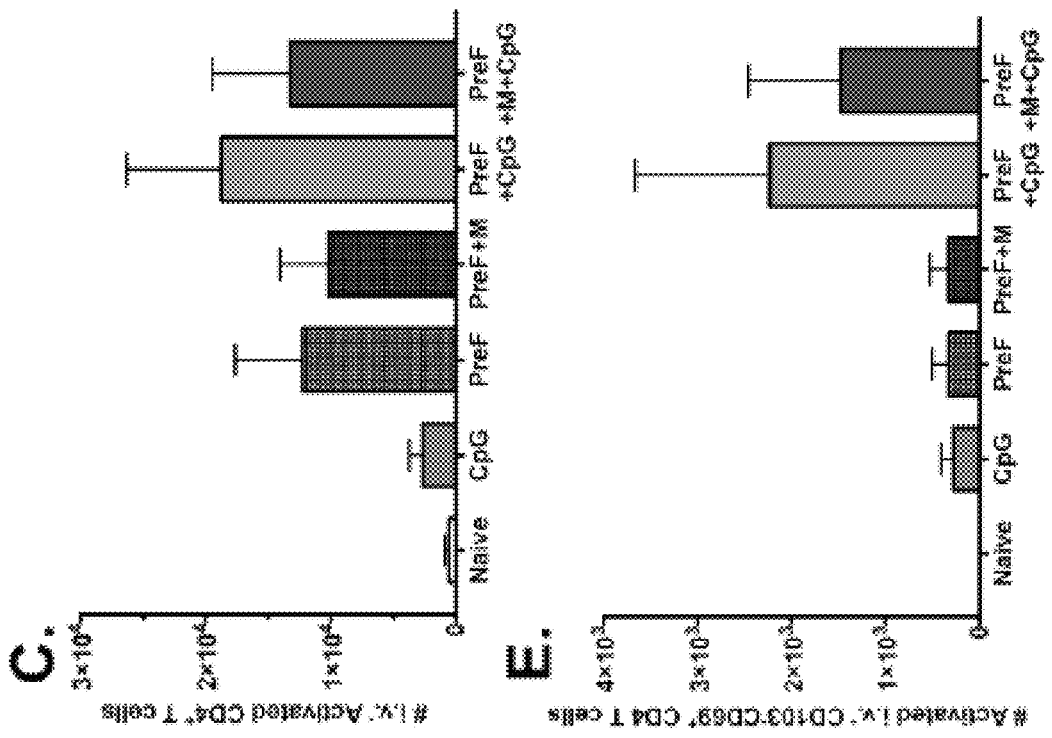
Figure 3:
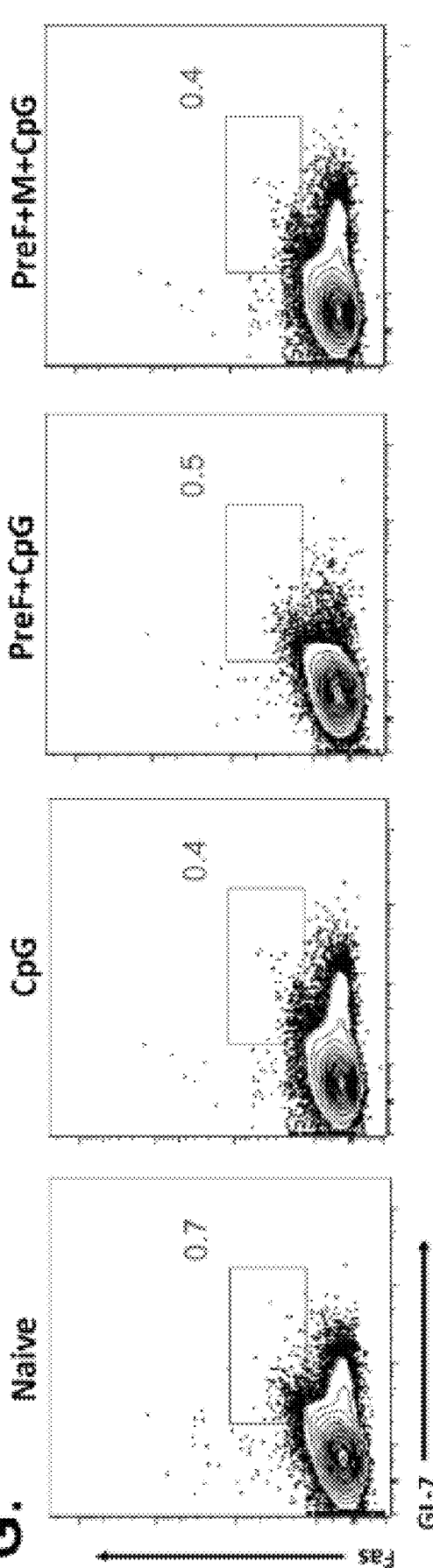

FIG. 3 illustrates that initial priming vaccination with prefusion RSV F induces lung-resident CD4 and CD8 T cells. BALB/c mice were primed with 500 μg of the indicated nanoparticle formulation or PBS (naïve) i.n. on day 0. Lungs and spleen were harvested on day 8 and analyzed by flow cytometry. The frequency of activated ($CD11a^{hi}CD49d^+$) CD4 T cells and activated ($CD11a^{hi}CD8^{lo}$) CD8 T cells was assessed as indicated in FIGS. 3A and 3B. The number of i.v.⁻CD4 and i.v.⁻CD8 T cells was assessed as indicated in FIGS. 3C and 3D. The number of activated i.v.⁻ $CD103^-CD69^+$ CD4 T cells and $CD103^+CD69^+$ CD8 T cells was assessed as indicated on FIGS. 3E and 3F. The representative flow cytometry plots of germinal center B cells ($CD19^+CDB220^+Fas^{+GL-7+}$) is illustrated in FIG. 3G.

Figure 4:
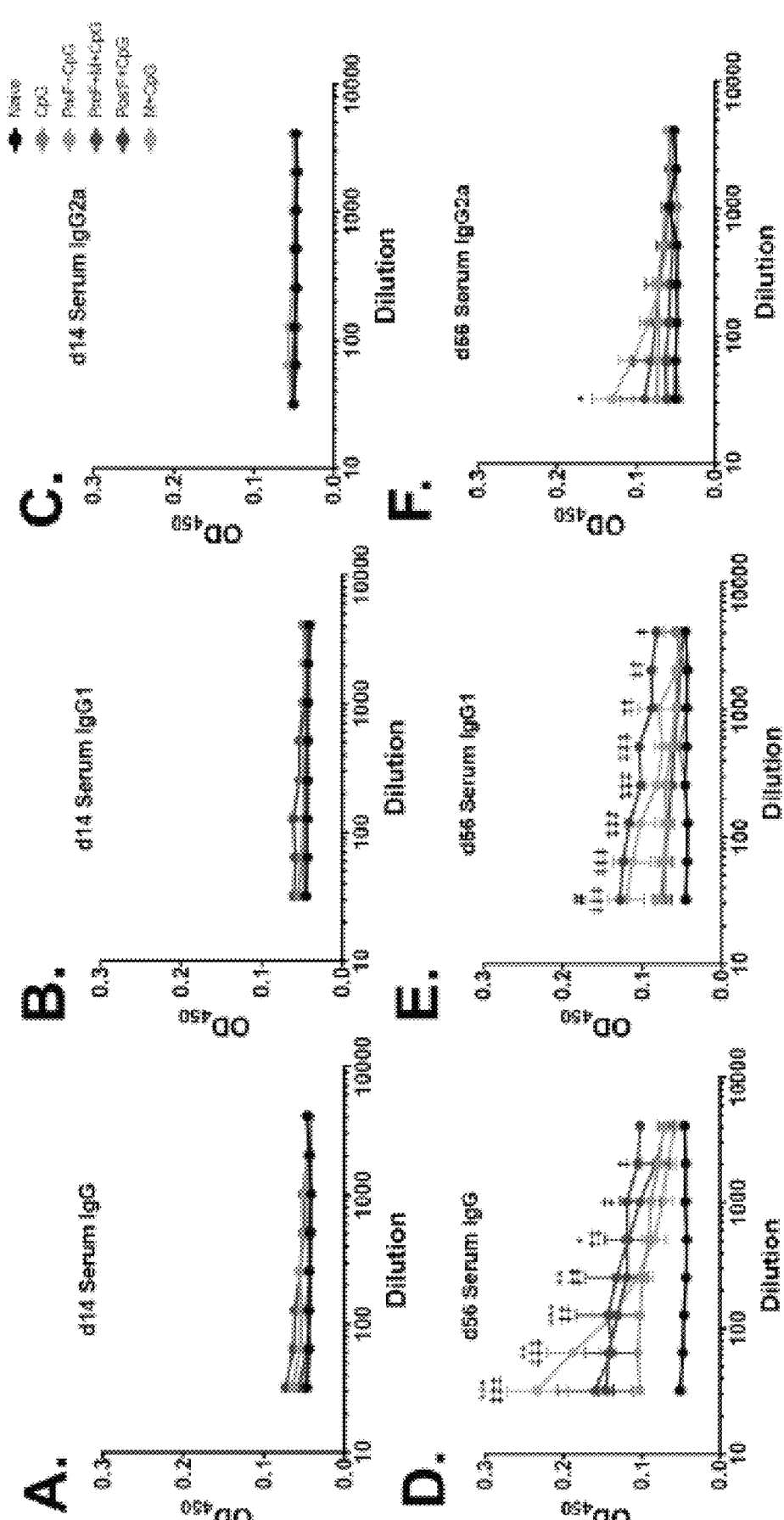

FIG. 4 illustrates that a prime/boost nanoparticle vaccination induces RSV-specific antibodies in serum. BALB/c mice were primed with 500 μg of the indicated nanoparticle formulation i.n. on day 0, and boosted with 500 μg i.n. on day 28. Control mice (labeled naïve) were administered PBS i.n. on both prime and boost days. On day 14 and 56 serum was assessed for total RSV-specific IgG, IgG1, or IgG2a.

Figure 5:
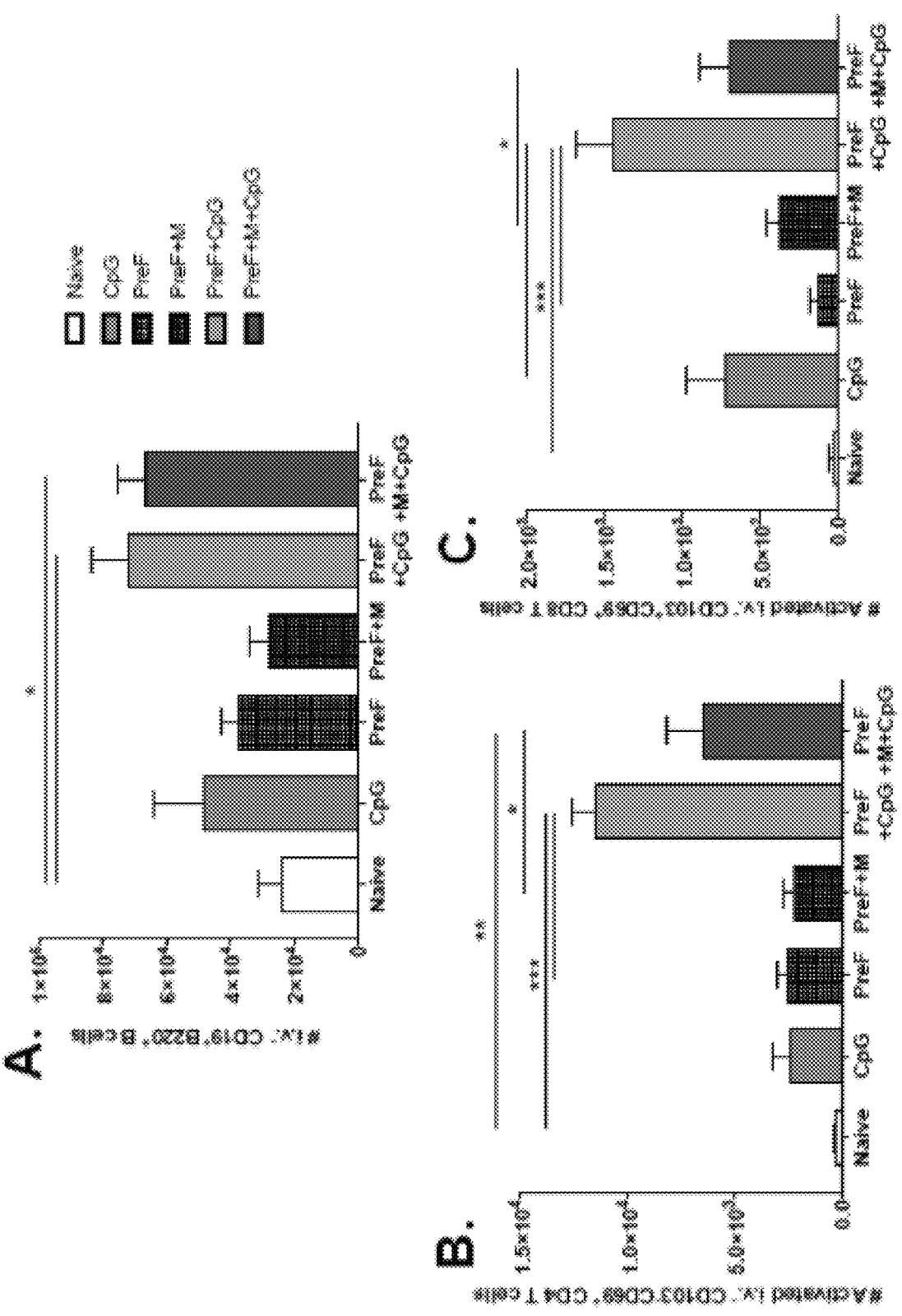
FIG. 5. Prime/boost nanoparticle vaccination with prefusion RSV F induces lung-resident B cells, CD4, and CD8 T cells. BALB/c mice were primed with 500 µg of the indicated nanoparticle formulation or PBS (naïve) i.n. on day 0, and boosted with 500 µg i.n. on day 28. Lung and spleen were harvested on day 42 and analyzed by flow cytometry. (A) Number of i.v.$^{-}$ B cells. Number of activated i.v.$^{-}$ (B) CD103$^{-}$CD69$^{+}$ CD4 T cells and (C) CD103$^{+}$CD69$^{+}$CD8 T cells. Number of activated (D) IFN-γ$^{+}$ CD4 T cells and (E) IL-5$^{+}$CD4 T cells following stimulation with PMA/ionomycin. Data are represented as mean±SEM from a single experiment (n=4 mice). Asterisks represent significance between naive and prefusion F+M+CpG, and ‡ represents significance between naive and postfusion F+CpG as determined by a one-way ANOVA with Tukey's post hoc test. *p<0.05, p<0.01, *p<0.001.
Figure 5:
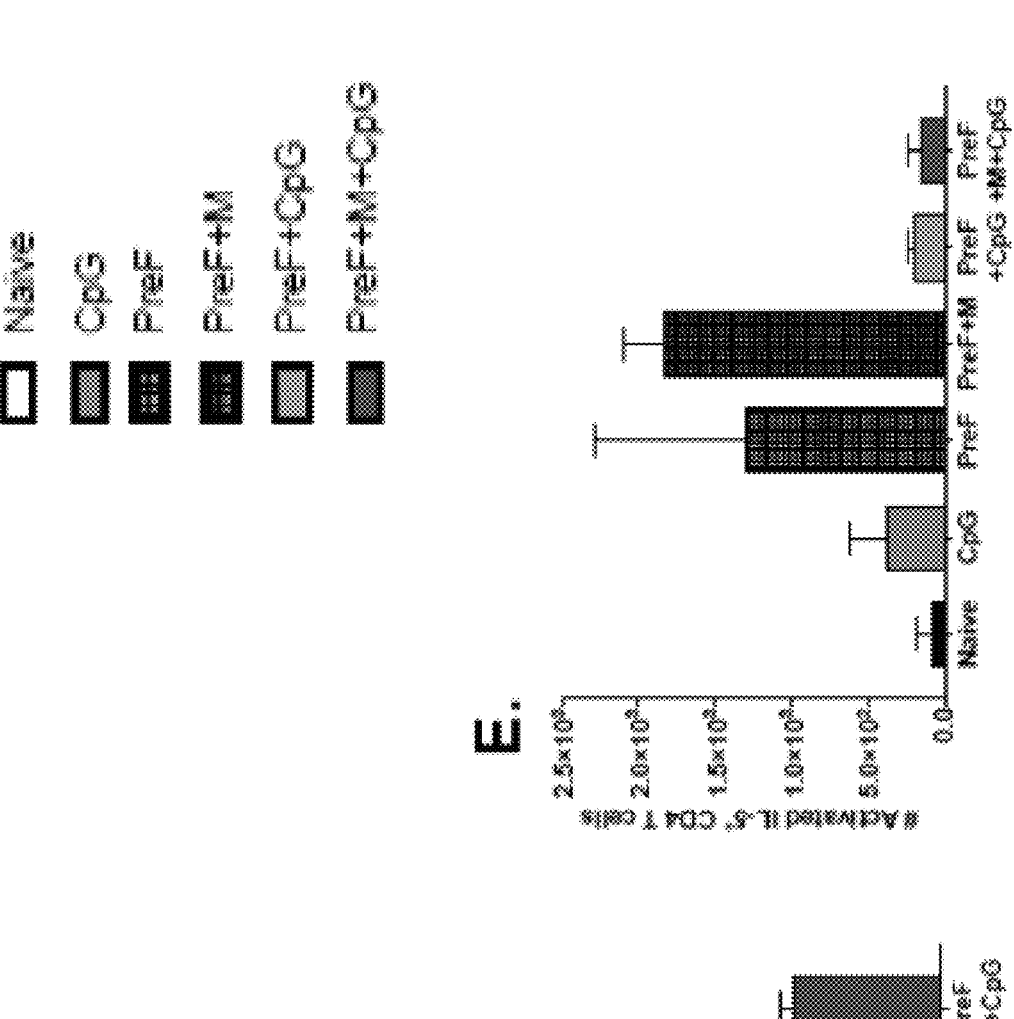

FIG. 5 illustrates that a prime/boost nanoparticle vaccination with prefusion RSV F induces lung-resident B cells, CD4, and CD8 T cells. BALB/c mice were primed with 500 μg of the indicated nanoparticle formulation or PBS (naïve) i.n. on day 0, and boosted with 500 μg i.n. on day 28. Lung and spleen were harvested on day 42 and analyzed by flow cytometry. We assessed the number of i.v.⁻ B cells, the number of i.v.⁻ activated CD103⁻CD69⁺ CD4 T cells and CD103⁺CD69⁺ CD8 T cells. We also assessed the number of activated IFN-γ⁺CD4 T cells and IL-5⁺ CD4 T cells following stimulation with PMA/ionomycin.

CONCLUSION

Prime/boost nanoparticle vaccination with a prefusion RSV F nanoparticle-based vaccine reduced weight loss, pulmonary dysfunction, and viral copy numbers following an RSV challenge. Priming vaccination alone was shown to be sufficient to elicit i.v.⁻ tissue-resident CD4 and CD8 T cells. Prime/boost nanoparticle vaccination generated RSV-specific antibodies in serum, and prime/boost vaccination elicited IFN-γ⁺ CD4 T cells and tissue-resident T and B cells.

There are numerous benefits to the RSV vaccine as prepared by the inventors. First, the inventors' nanoparticle formulation allows for continual, controlled release of the antigen(s). Second, the inventors' nanoparticle formulation includes the F protein in a pre-fusion stabilized form, which allows for better exposure of the major RSV F antigenic site (Ø) to a vaccinee's immune system. Third, the inventors' nanoparticle formulation induces robust B and T cell responses due to inclusion of both of the F protein in a pre-fusion stabilized form and the M protein.

Figure 6:
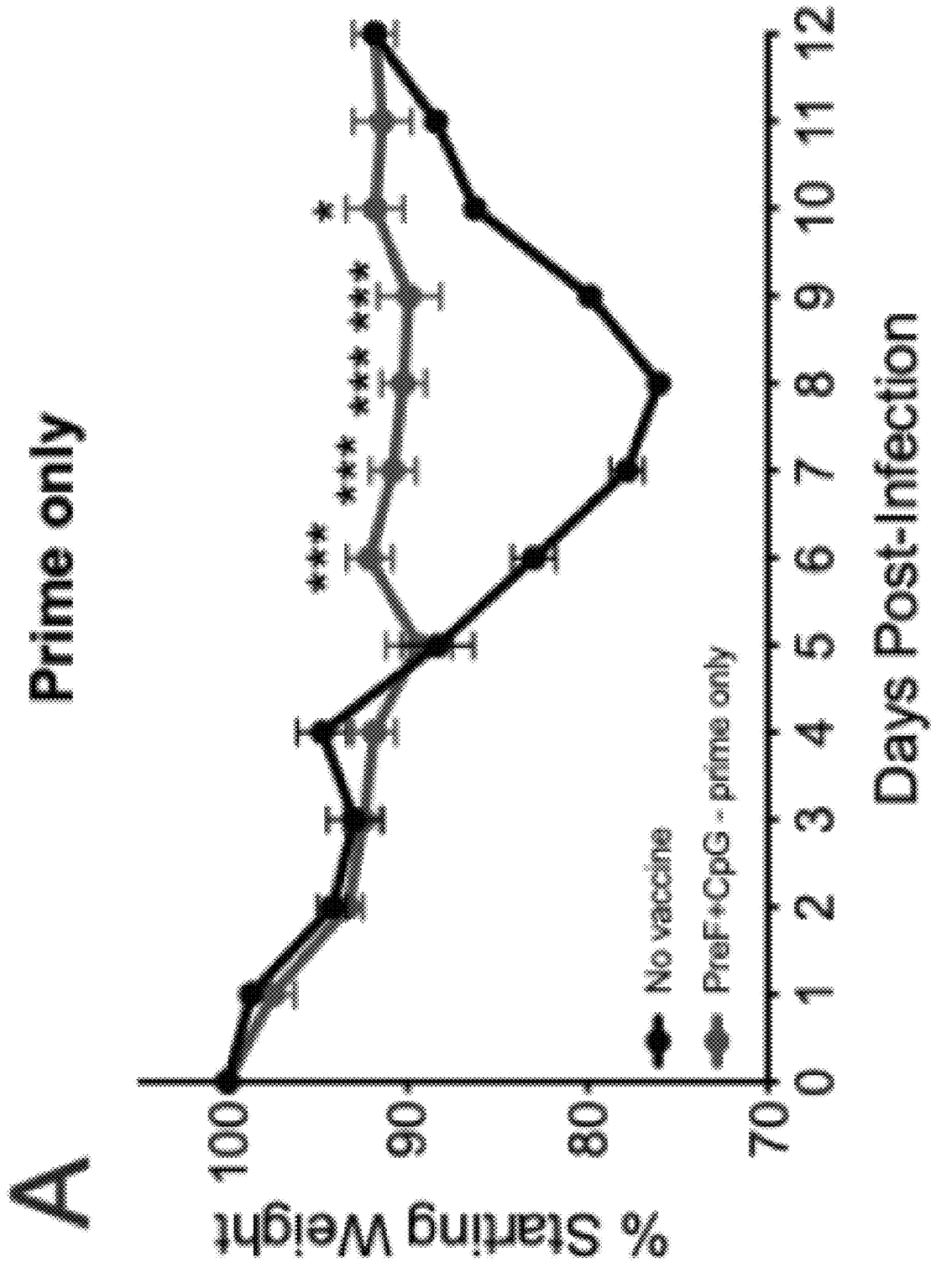
FIG. 6. Prime/boost nanoparticle vaccination with prefusion RSV F protects against RSV-induced weight loss and pulmonary dysfunction. (A-B) BALB/c mice were primed with 500 µg of the indicated nanoparticle formulation i.n. on day 0, and challenged with 4.8×10$^{6}$ PFU RSV-A2 i.n. on day 28. No vaccine mice were administered PBS i.n. at the prime. Groups were monitored daily for (A) weight loss and (B) airway obstruction (Penh). (C-D) BALB/c mice were primed with 500 µg of the indicated nanoparticle formulation i.n. on day 0, and boosted with 500 µg i.n. on day 28. No vaccine mice were administered PBS i.n. on both prime and boost days. All mice were challenged with 4.8×10$^{6}$ PFU RSV-A2 i.n. on (C-D) day 56 or (E-F) day 100 and assessed for weight loss and airway obstruction (Penh). Asterisks represent significance between no vaccine and preF+CpG and pound symbols represent significance between CpG and preF+CpG as determined by (A-B) Student t test, or (C-F) 2-way ANOVA with Dunnett's post hoc test. *$^{/#}$p<0.05, $^{/##}$p<0.01, *$^{/###}$p<0.001.
Figure 6:
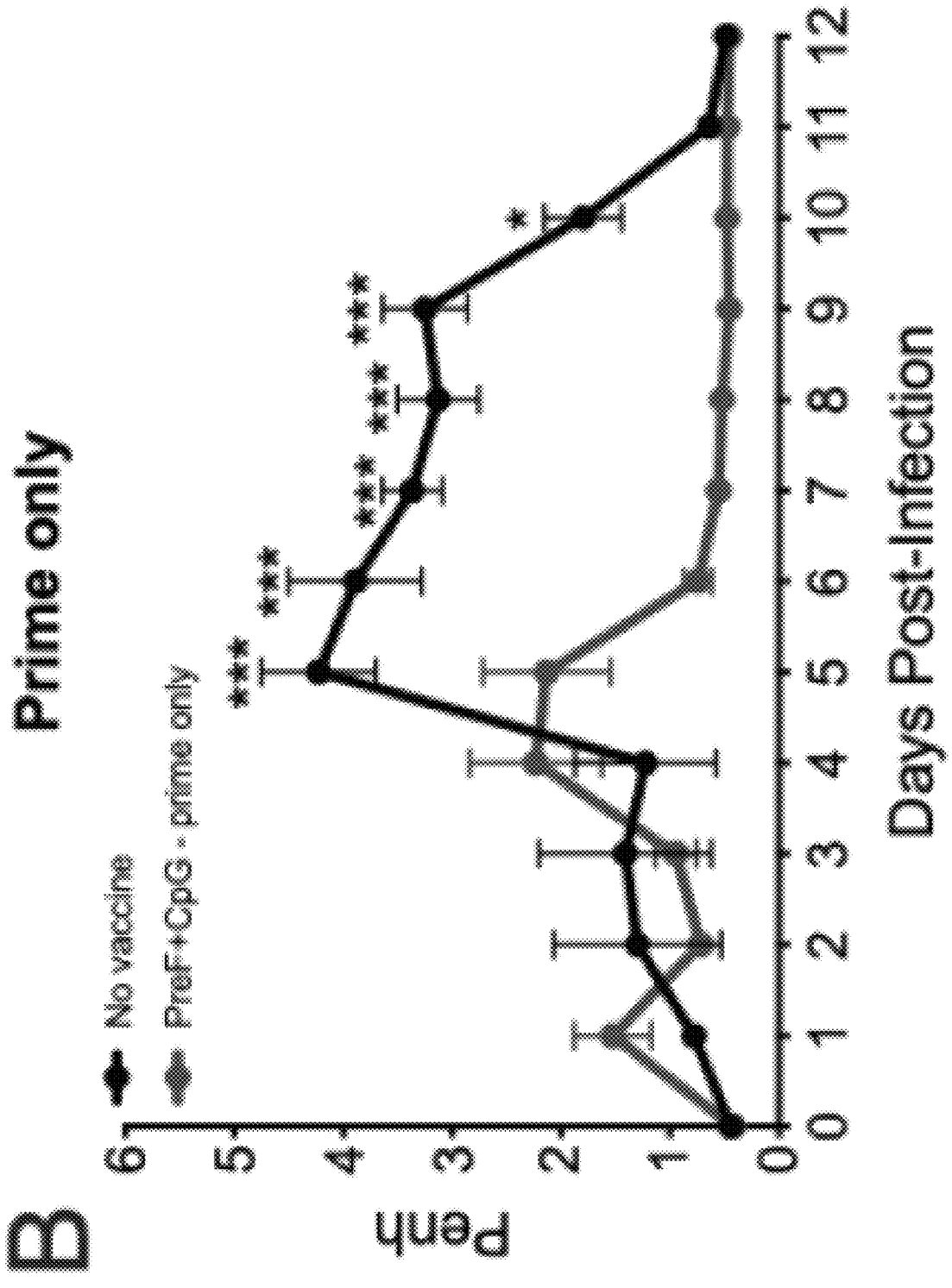
Figure 6:
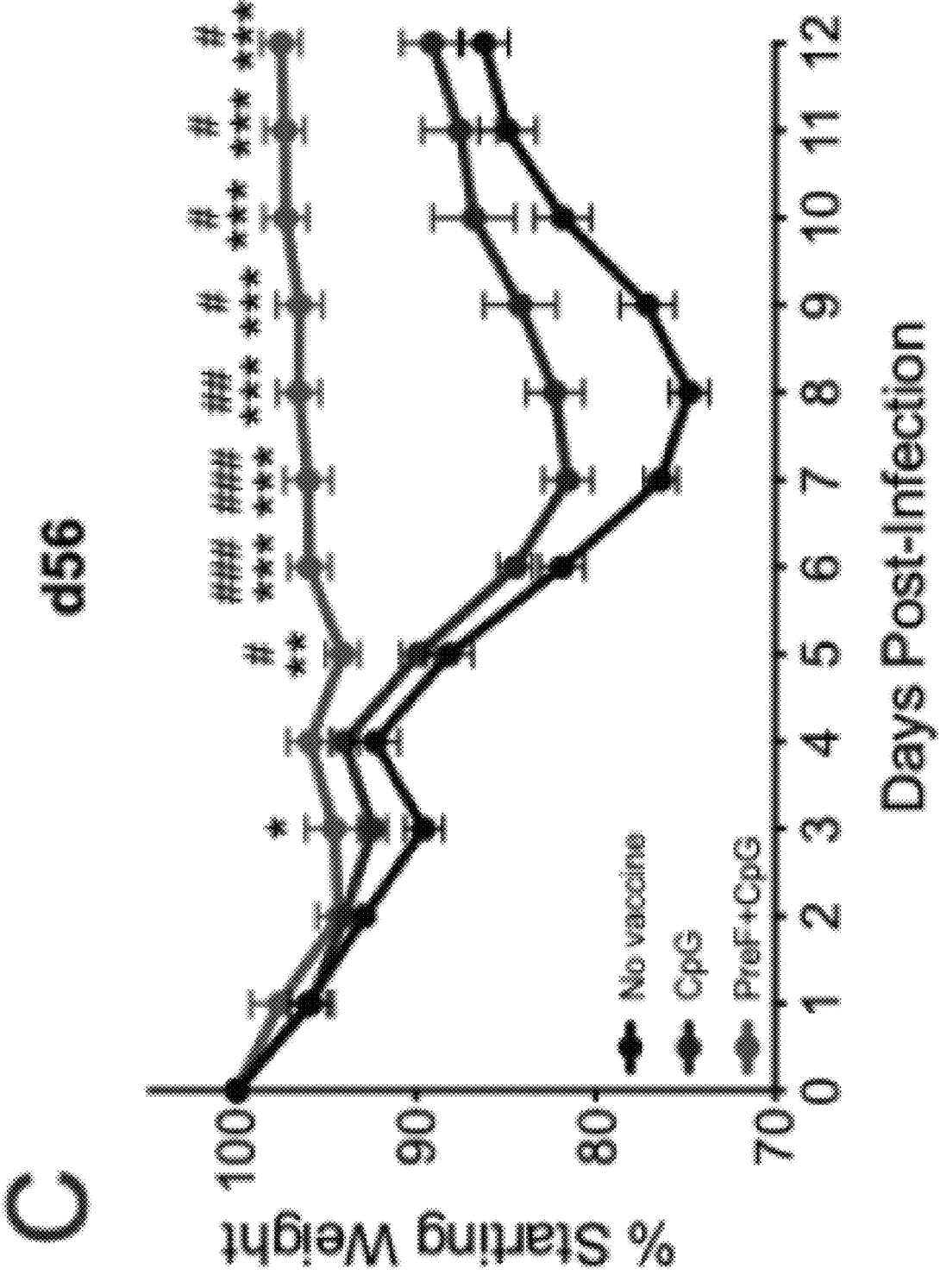
Figure 6:
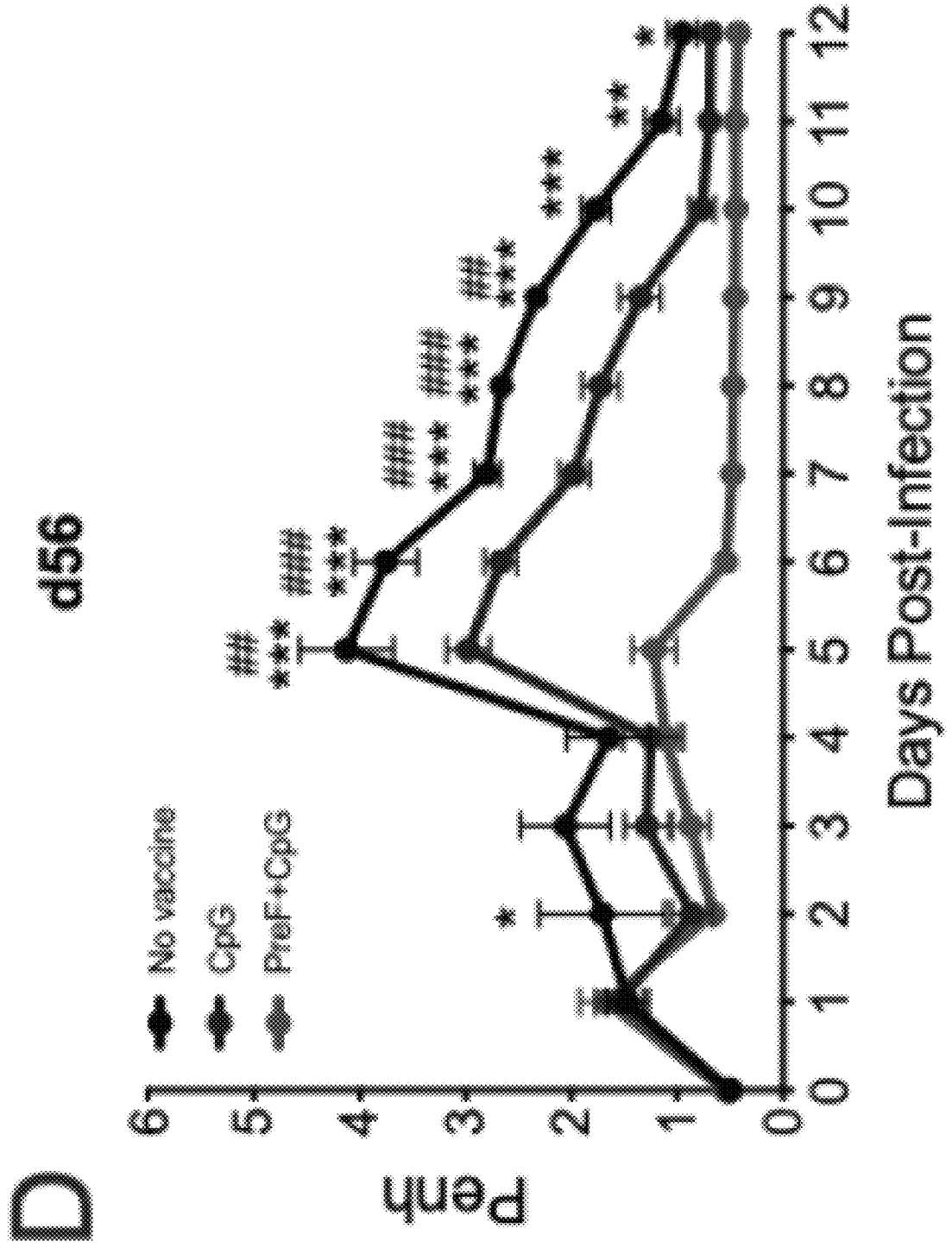
Figure 6:
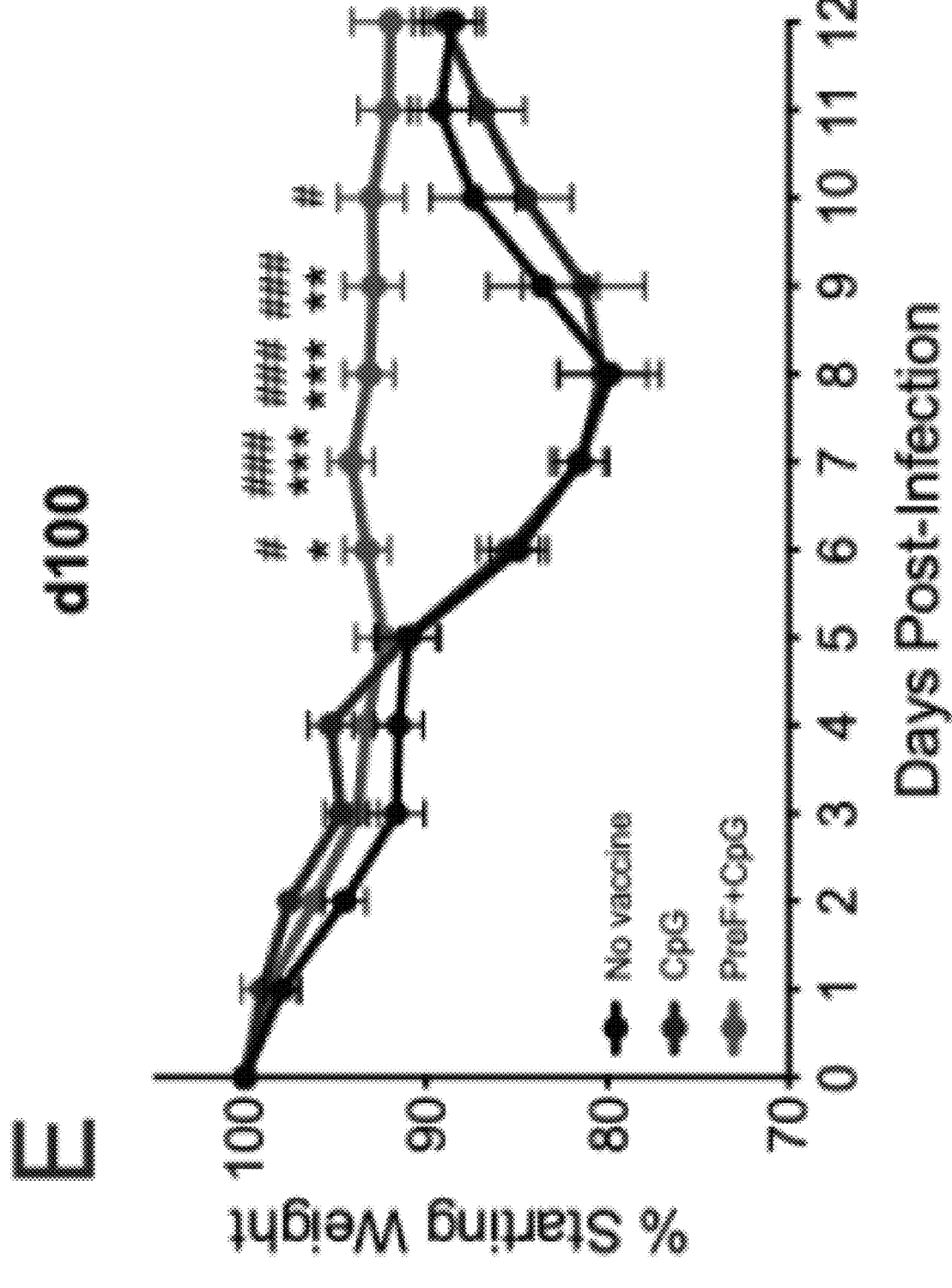
Figure 6:
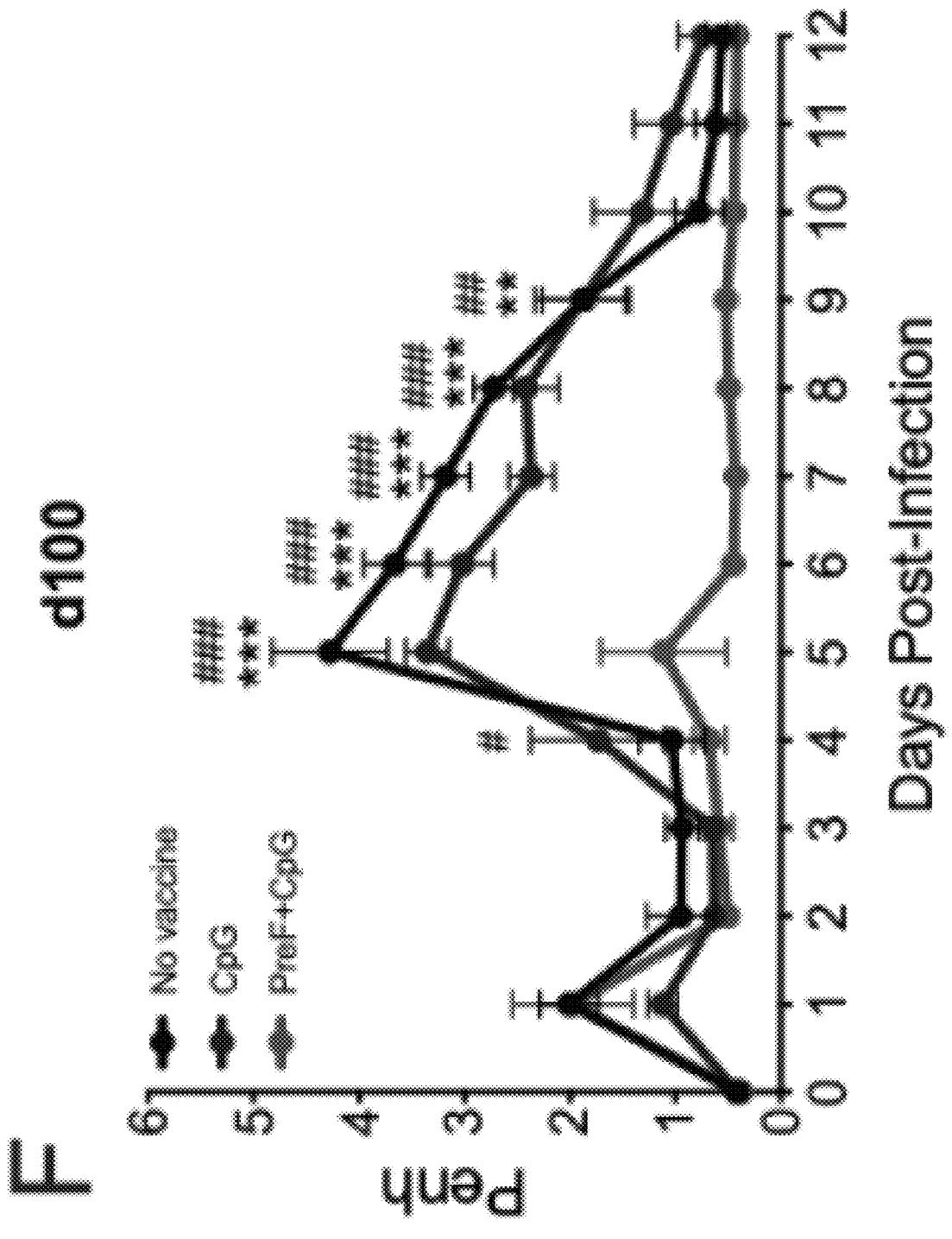

Example 2—Protection Against RSV-Induced Disease by Nanoparticle Formulation Containing RSV Pre-F Protein and CpG Adjuvant Our data demonstrate that a single prime only immunization with the nanoparticle formulation containing RSV pre-F+CpG adjuvant is sufficient to provide protection against RSV-induced disease including weight loss and airway dysfunction (e.g Penh) as compared to unimmunized control mice or mice immunized with nanoparticles containing the CpG adjuvant only (without the PreF antigen). (See FIG. 6). Prime only immunization is also sufficient to significantly reduce virus replication in the lung as compared to unimmunized mice or mice immunized with nanoparticles containing the CpG adjuvant only (without the PreF antigen). Mice immunized using a prime/boost immunization approach also exhibit significant protection against RSV-induced disease including weight loss and airway dysfunction (e.g Penh) as compared to unimmunized mice when challenged either at 56 days post-prime (see FIGS. 6C and 6D) or Day 100 post-prime (see FIGS. 6E and 6F).

Figure 7:
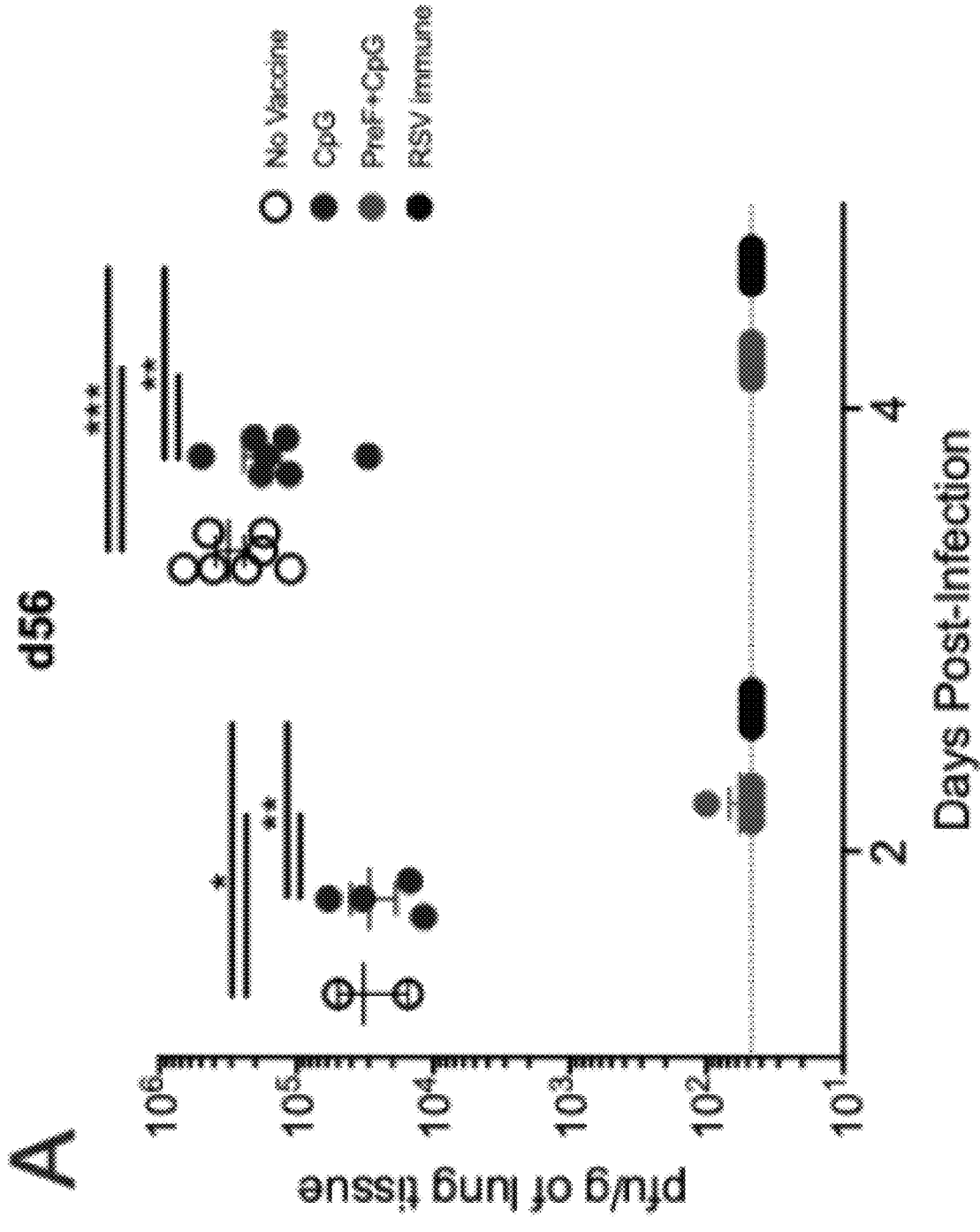
FIG. 7. Prime/boost nanoparticle vaccination with prefusion RSV F reduces infectious RSV particles. (A-B) BALB/c mice were primed with 500 µg of the indicated nanoparticle formulation i.n. on day 0, and boosted with 500 µg i.n. on day 28. No vaccine mice were administered PBS i.n. on both prime and boost days. RSV immune mice received 4.8×10$^{6}$ PFU RSV-A2 i.n. at the prime and PBS i.n. at the boost. On (A) day 56 or (B) day 100, all mice were challenged with 4.8×10$^{6}$ PFU RSV-A2 i.n and infectious plaque-forming units (pfu) were quantified in the lung on (A) day 2 or (A and B) day 4 by plaque assay. (C) BALB/c mice were primed with 500 µg of the indicated nanoparticle formulation i.n. on day 0, and challenged with 4.8×10$^{6}$ PFU RSV-A2 i.n. on day 28. No vaccine mice were administered PBS i.n., and RSV immune mice received 4.8×10$^{6}$ PFU RSV-A2 i.n. at the prime. On day 28, all mice were challenged with 4.8×10$^{6}$ PFU RSV-A2 i.n and infectious pfu were quantified in the lung on day 4 by plaque assay. Statistical significance was determined by (A) 2-way ANOVA or (B-C) one-way ANOVA with a Tukey's post hoc test. *p<0.05, p<0.01, *p<0.001.
Figure 7:
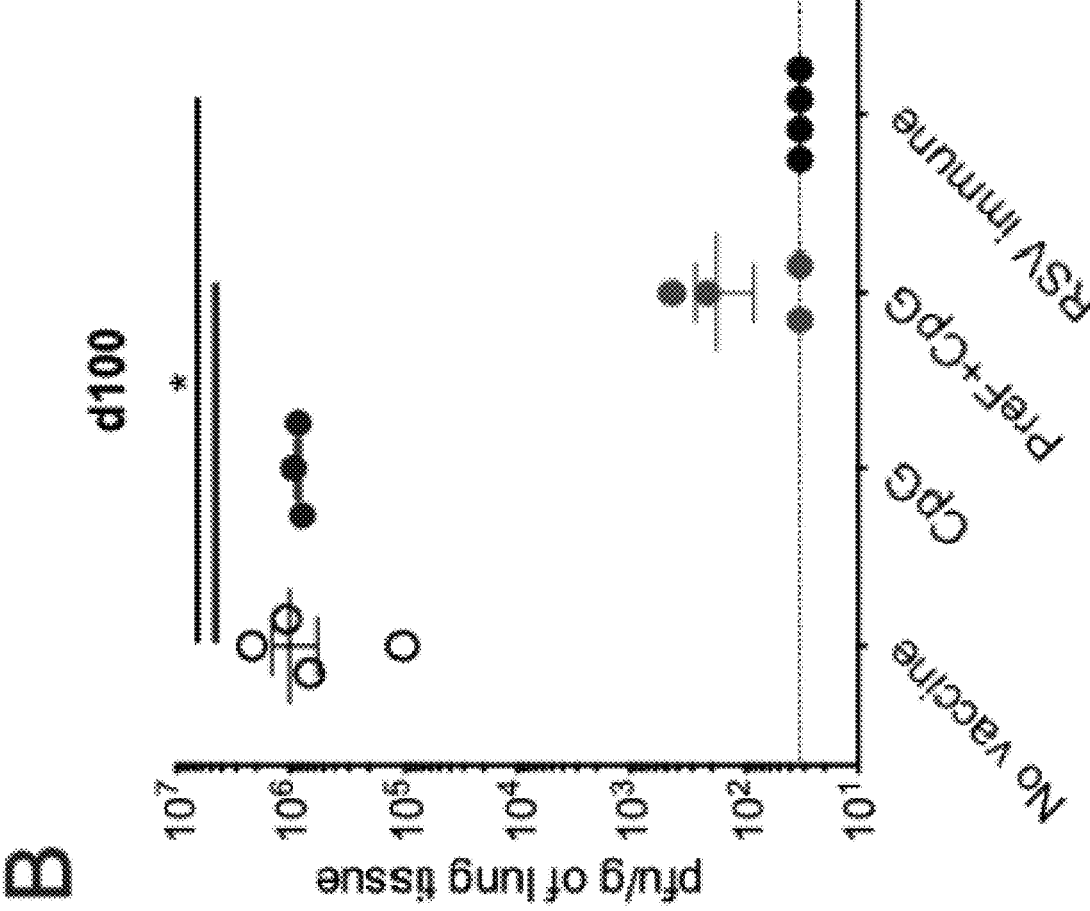
Figure 7:
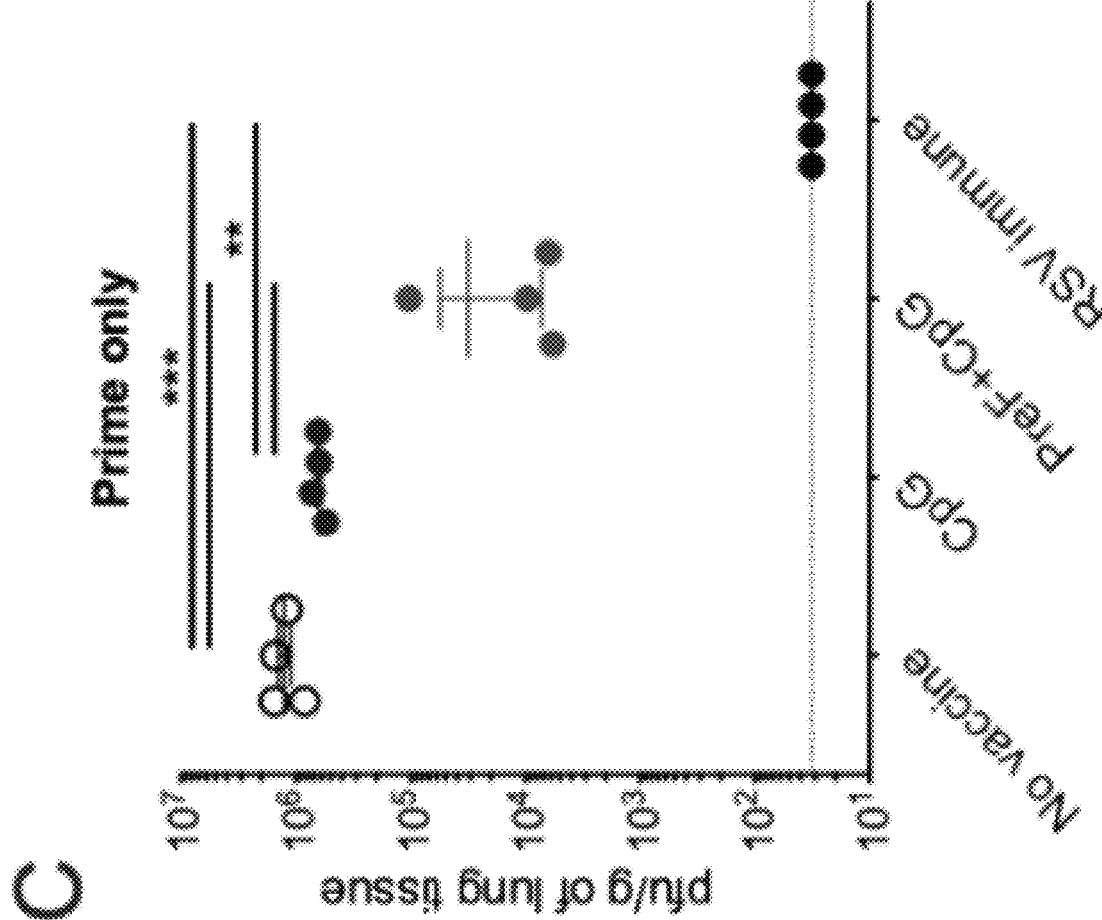

Mice that received a prime/boost immunization exhibited significantly reduced virus replication in the lung as compared to unimmunized mice or mice immunized with nanoparticles containing the CpG adjuvant only (without the PreF antigen) as shown in FIG. 7A (day 56 challenge) or FIG. 7B (day 100 challenge).

Figure 8:
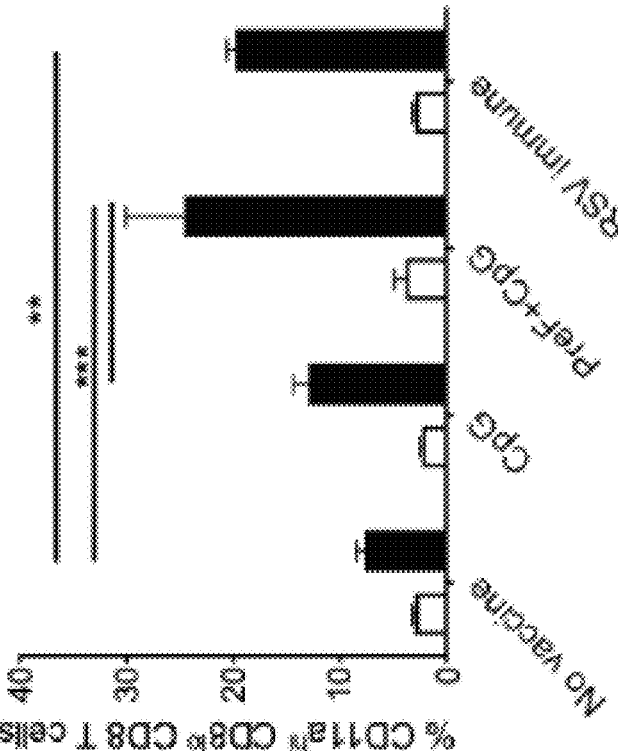
FIG. 8. Prime/boost nanoparticle vaccination with prefusion RSV F induces activated T cells in the lungs. BALB/c mice were primed with 500 µg of the indicated nanoparticle formulation i.n. on day 0, and boosted with 500 µg i.n. on day 28. No vaccine mice were administered PBS i.n. on both prime and boost days. RSV immune mice received 4.8×10$^{6}$ PFU RSV-A2 i.n. at the prime and PBS i.n. at the boost.
Figure 8:
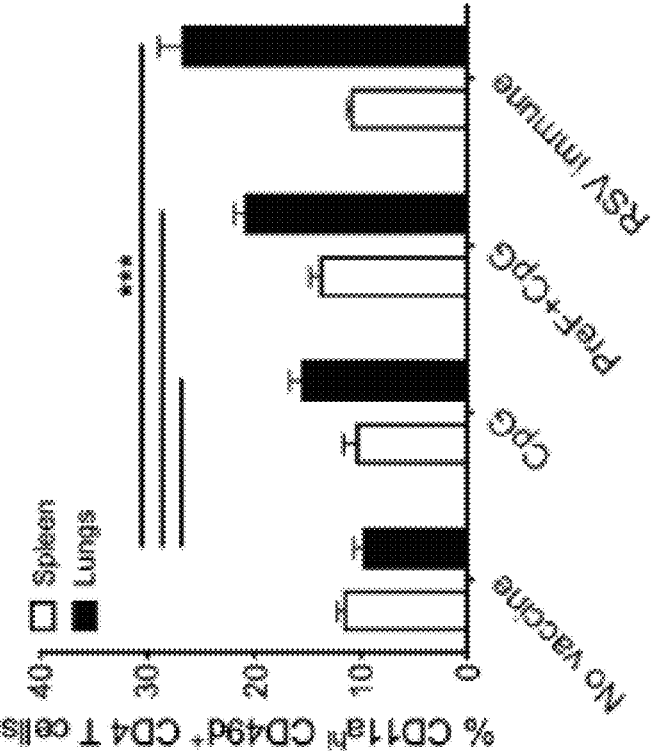

Our data indicate that prime/boost vaccination with PreF+CpG nanoparticles elicits an increase in activated CD4 and CD8 T cells as compared to mice immunized with nanoparticles containing only CpG or unimmunized mice (FIGS. 8A and 8B). This data is consistent with the induction of a T cell response following the nanoparticle vaccination.

Additional data indicate that the activated CD4 and CD8 T cells exhibit phenotypic cell surface markers (CD69⁺ for CD4 T cells and CD69⁺CD103⁺ for CD8 T cells) that is consistent with a tissue-resident population (e.g. Trm) that may be important in providing protection (FIGS. 9A and 9B). In addition, the activated CD4 and CD8 T cells make IFN-γ following stimulation indicating that they are of a Th1 and Tc1 phenotype, respectively (FIGS. 9C and 9D).

Using MHC-class I tetramers to identify RSV-specific CD8 T cells, we observed a significant increase in the total number of RSV tetramer-specific CD8 T cells specific to the F85-93 CD8 T cell epitope 2 weeks following the boost immunization (eg day 42 post-prime) as compared to unimmunized mice or mice immunized with nanoparticles containing the CpG adjuvant only (without the PreF antigen) as shown in FIG. 9E. FIG. 9F shows that these RSV tetramer-staining cells are located in the lung tissue.

FIG. 10 represents additional data demonstrating that mice immunized using a prime/boost immunization approach exhibit significant protection against RSV-induced airway dysfunction (e.g EF50) as compared to unimmunized mice when challenged either at 56 days post-prime (FIG. 5A) or at 100 days post-prime (FIG. 5B). FIG. 5C demonstrates additional data showing that mice immunized using a prime/boost immunization approach using PreF+CpG nanoparticles exhibit significant protection against RSV replication as measured by RT-PCR for the RSV N gene as compared to mice immunized with nanoparticles containing only CpG or unimmunized mice.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/ or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A vaccine composition comprising
   a) an effective amount of respiratory syncytial virus (RSV) F protein in a pre-fusion stabilized form and RSV M protein,
   b) a CpG oligonucleotide, and
   c) biodegradable polyanhydride polymer particles formed from a 1,ω-bis(p-carboxyphenoxy)($C_2$-$C_{12}$)alkane, a 1,ω-bis(p-carboxyphenoxy)($C_2$-$C_{12}$)dioxa-alkane, and a ($C_5$-$C_{20}$)alkanoic diacid,
   wherein the pre-fusion stabilized RSV F protein and RSV M protein, and the CpG oligonucleotide are incorporated into the biodegradable polyanhydride polymer particles for inducing an immune response against RSV.

2. The vaccine composition of claim 1, wherein the F protein in a pre-fusion stabilized form is selected from the group consisting of DS-Cav1, DS-TriC, Vav-1-TriC, DX-Cav1-TriC, Pre-F-GCN4t, SC-DM, and SC-TM.

3. The vaccine composition of claim 2, wherein the F protein in a pre-fusion stabilized form is DS-Cav1.

4. The vaccine composition of claim 1, wherein the CpG oligonucleotide is a CpG oligodeoxynucleotide (ODN).

5. The vaccine composition of claim 1, wherein the vaccine composition induces an antibody response and a CD4 T cell response when administered to a subject in need thereof.

6. The vaccine composition of claim 1, wherein the polymer is formed from 1,6-bis(p-carboxyphenoxy)hexane (CPH), 1,8-bis(p-carboxyphenoxy)-3,6-dioxaoctance (CPTEG), and sebacic acid (SA).

7. The vaccine composition of claim 6, wherein the CPH and CPTEG are at a ratio range of CPH:CPTEG of 80-60: 20-40.

8. The vaccine composition of claim 1, further comprising an RSV protein selected from NS1, NS2, N, P, SH, G, M2-1, M2-2, L, or any combinations thereof.

9. A method comprising administering the vaccine composition of claim 1 at least once to a subject who is at risk for infection by RSV.

10. The method of claim 9, wherein after the vaccine composition is administered to the subject, the subject is protected against infection by RSV.

11. The method of claim 9, wherein the vaccine composition is administered by a route selected from intranasal, pulmonary, oral, subcutaneous, intramuscular, or intravenous.

12. The method of claim 9, wherein the vaccine composition reduces RSV replication in the subject.

13. The method of claim 9, comprising administering the vaccine composition to the subject a second time after the first administration of the vaccine.

14. The method of claim 13, wherein the subject is protected against infection by RSV and the protection is effective upon exposure to RSV.

15. The method of claim 13, wherein the vaccine composition reduces RSV replication in the subject.

16. The method of claim 14, wherein the vaccine composition induces CD4 T cells, CD8 T cells, and B cells in the subject.

17. The method of claim 14, wherein the vaccine composition induces long-term immunity to RSV infection.

18. A method comprising administering a vaccine composition to a subject who is at risk for infection by RSV, the vaccine composition comprising:
   a) an effective amount of respiratory syncytial virus (RSV) F protein in a pre-fusion stabilized form,
   b) a CpG oligonucleotide, and
   c) biodegradable polvanhydride polymer particle formed from a 1,ω-bis(p-carboxyphenoxy)($C_2$-$C_{12}$)alkane, a 1,ω-bis(p-carboxyphenoxy)($C_2$-$C_{12}$)dioxa-alkane, and a ($C_5$-$C_{20}$)alkanoic diacid,
   wherein the pre-fusion stabilized RSV F protein and the CpG oligonucleotide are incorporated into the biodegradable polyanhydride polymer particles, wherein the vaccine composition is administered at least once to the subject, and wherein administration of the vaccine composition induces an immune response against RSV in the subject that protects against infection by RSV and the protection is effective upon exposure to RSV.

19. The method of claim 18, wherein the vaccine composition induces CD4 T cells, CD8 T cells, and B cells in the subject.

20. The method of claim 18, wherein the vaccine composition induces long-term immunity to RSV infection.

\* \* \* \* \*

SEQUENCE LISTING

<160> NUMBER OF SEQ ID NOS: 12

<210> SEQ ID NO 1
<211> LENGTH: 15277
<212> TYPE: DNA

-continued

<213> ORGANISM: Human Respiratory Syncytial Virus

<400> SEQUENCE: 1

```
acgcgaaaaa atgcgtacaa caaacttgcg taaaccaaaa aaatggggca aataagaatt      60
tgataagtac cacttaaatt taactccttt ggttagagat gggcagcaac tcattgagta     120
tgataaaagt tagattgcaa aatctgtttg acaatgatga agtagcattg ttaaaaataa     180
catgctatac tgacaaatta atacagttaa ctaatgcttt ggctaaggca gttatacata     240
caatcaaatt gaatggcatt gtatttgtgc atgttattac aagtagtgat atttgcccta     300
ataataatat tgtagtgaaa tccaatttca caacaatgcc agtattacaa aatggaggtt     360
atatatggga aatgatggaa ttaacacact gctctcaacc taatggccta atagatgaca     420
attgtgaaat taaattctcc aaaaaactaa gtgattcaac aatgaccaat tatatgaatc     480
aattatctga attacttgga tttgacctca atccataaat cataataaat atcaactagc     540
aaatcaatgt cactaacacc attagttaat ataaaacttg acagaagata aaaatggggc     600
aaataaatcg attcagccga cccaaccatg gacacaacac acaatgatac cacaccacaa     660
agactgatga tcacagacat gagaccatta tcgcttgaga ctataataac atctctaacc     720
agagatatca taacacataa atttatatac ttgataaatc atgaatgcat agtgagaaaa     780
cttgatgaaa gacaggccac atttacgttt ctggtcaact atgaaatgaa actattgcac     840
aaagtgggaa gcactaaata taaaaaatat actgaataca cacaaaaata tggcactttc     900
cctatgccaa tatttatcaa tcatgatggg ttcttagaat gcattggcat taagcctacc     960
aagcacacac ccataatata caagtatgat ctcaatccat gaatatcaaa ccaagattca    1020
aacaatccga ataacaact ttatgcataa tcacactcca tagtccagat ggagcctgaa     1080
aattatagtt atttaaaatt aaggagagac ataagatgaa agatggggca aatacaaaaa    1140
tggctcctag caaagtcaag ttgaatgata cactcaacaa agatcaacct ccatcatcca    1200
gcaaatatac catccaacgg agcacaggag acagcaccga cactcccaat tatgatgtgc    1260
agaaacacac caataagcta tgtggcatgt tattaatcac agaagatgct aatcataaat    1320
tcactgggtt aataggtatg ttatatgcta tgtctagatt aggaagagaa gacaccataa    1380
aaatactcaa agatgcggga tatcatgtta aggcaaatgg agtggatgta acaacacatc    1440
gtcaagacat taatgggaaa gaaatgaaat ttgaagtgtt aacattagca agcttaacaa    1500
ctgaaattca aatcaacatt gagatagaat ctagaaaatc ctacaaaaaa atgctaaaag    1560
aaatgggaga ggtggctcca gaatacaggc atgactctcc tgattgtggg atgataatat    1620
tatgtatagc agcattagta ataaccaaat tagcagcagg agatagatca ggtcttacag    1680
ctgtgattag gagagctaat aatgtcctaa aaaatgaaat gaaacgttat aaaggtttat    1740
tacccaagga tatagccaac agcttctatg aagtgtttga aaaatatcct cactttatag    1800
atgtttttgt tcattttggt atagcacaat cttctaccag aggtggcagt agagttgaag    1860 ggattttttgc aggattgttt atgaatgcct atggtgcagg gcaagtgatg ttacggtggg    1920
gggtcttagc aaaatcagtt aaaaacatta tgttaggaca cgctagtgta caagcagaaa    1980
tggaacaagt tgtggaggtg tatgagtatg ctcagaaatt gggtggagaa gcaggattct    2040
accatatatt gaacaaccca aaagcatcac tattatcttt gactcaattt cctcacttct    2100
ctagtgtagt attgggcaat gctgctggcc taggcataat gggagaatac agaggtacac    2160
caaggaatca gatttatat gatgctgcaa aagcatatgc tgaacaactc aaagaaaatg    2220
gtgtgattaa ctacagtgta ttagatttga cagcagaaga actagaggct atcaaacatc    2280
```

-continued

```
agcttaatcc aaaagataat gatgtagagc tttgagttaa taaaaaggtg gggcaaataa      2340
atcatcatgg aaaagtttgc tcctgaattc catggagaag atgcaaacaa cagagccacc      2400
aaattcctag aatcaataaa gggcaaattc acatcaccca aagatcccaa gaaaaaagat      2460
agtatcatat ctgtcaactc aatagatata gaagtaacca aagaaagccc tataacatca      2520
aattcaacca ttataaaccc aataaatgag acagatgata ctgtagggaa caagcccaat      2580
tatcaaagaa agcctctagt aagtttcaaa gaagaccota cgccaagtga taatcctttt      2640
tcaaaactat acaaagaaac catagaaaca tttgataaca atgaagaaga atctagctat      2700
tcatatgaag aaataaatga tcagacaaac gataatataa cagcaagatt agataggatt      2760
gatgagaaat taagtgaaat actaggaatg cttcacacat tagtagtagc gagtgcagga      2820
cccacatctg ctcgggatgg tataagagat gccatggttg gtttaagaga agaaatgata      2880
gaaaaaatca gaactgaagc attaatgacc aatgacagac tagaagctat ggcaagactc      2940
aggaatgaag aaagtgaaaa gatggcaaaa gacacatcag atgaagtgtc tctcaatcca      3000
acatcagaga aactgaacaa cctgttggaa gggaatgata gtgacaatga tctatcactt      3060
gaagatttct gattagctac caaactgtac atcaaaacac aacaccaata gaaaaccaac      3120
aaacaaacca actcacccat ccaaccaaac atctatctgc tgattagcca accagccaaa      3180
aaacaaccag ccaatctaaa actagccacc cggaaaaaat cgatactata gttacaaaaa      3240
aagatggggc aaatatggaa acatacgtga ataaacttca cgagggctcc acatacacag      3300
ctgctgttca atacaatgtc ctagaaaaag acgatgatcc tgcatcactt acaatatggg      3360
tgcccatgtt ccaatcatcc atgccagcag atctactcat aaaagaacta gccaatgtca      3420
atatactagt gaaacaaata tccacaccca agggaccctc attaagagtc atgataaact      3480
caagaagtgc agtgctagca caaatgccca gcaaatttac catatgtgcc aatgtgtcct      3540
tggatgaaag aagcaagctg gcatatgatg taaccacacc ctgtgaaatt aaggcatgca      3600
gtctaacatg cctaaaatca aaaaatatgt taactacagt taaagatctc actatgaaaa      3660
cactcaaccc aacacatgac atcattgctt tatgtgaatt tgaaaatata gtaacatcaa      3720
aaaaagtcat aataccaaca tacctaagat ctatcagcgt cagaaataaa gatctgaaca      3780
cacttgaaaa tataacaacc actgaattca aaaatgccat tacaaatgca aaaatcatcc      3840
cttactcagg attactgtta gtcatcacag tgactgacaa caaaggagca ttcaaataca      3900
taaagccaca aagtcaattc atagtagatc ttggagctta cctagaaaaa gaaagtatat      3960
attatgttac aacaaattgg aagcacacag ctacacgatt tgcaatcaaa cccatggaag      4020
attaaccttt ttcctctaca ttaatgagta gattcataca aactttctaa ctacattctt      4080
cacttcacaa tcataatcac caaccctctg tggttcaatc aatcaaacaa aactcatcag      4140
gagttccaga tcatcccaag tcattgttca tcagatccag tactcaaata agttaataaa      4200
aaatccacat ggggcaaata atcattgagg gtaatccaac taatcacaac atctgtcaac      4260
atagacaagt caacacgcta gataaaatca accaatggaa aatacatcca taactataga      4320
attctcaagc aaattctggc cttactttac actaatacac atgataacaa caataatctc      4380
tttgataatc ataatctcca tcatgattgc aatactaaac aaactctgcg aatataatgt      4440
attccataac aaaacctttg agctaccaag agctcgagtc aatacatagc atttaccaat      4500
ctgatagctc aaaacagtaa ccttgcattt gtaaatgaac taccctcact tcttcacaaa      4560
accacatcaa catctcacca tgcaagccat catctatacc ataaagtagt taattaaaaa      4620
```

-continued

```
atagtcataa caatgaacta ggatattaag accaaaaaca acgctggggc aaatgcaaac    4680
atgtccaaaa ccaaggacca acgcaccgcc aagacactag aaaggacctg ggacactctc    4740
aatcatctat tattcatatc atcgtgctta tacaagttaa atcttaaatc tatagcacaa    4800
atcacattat ctattttggc aatgataatc tcaacctcac ttataattgc agccatcata    4860
ttcatagcct cggcaaacca caaagtcaca ctaacaactg caatcataca agatgcaacg    4920
aaccagatca agaacacaac cccaacatac ctcactcaga atcccagct tggaatcagc    4980 ttctccaatc tgtccggaac tacatcacaa tccaccacca tactagcttc aacaacacca    5040
agtgctgagt caaccccaca atccacaaca gtcaagatca aaaacacaac aacaacccaa    5100
atattaccta gcaaacccac cacaaaacaa cgccaaaata aaccacaaaa caaacccaac    5160
aatgattttc actttgaagt gttcaatttt gtaccctgca gcatatgcag caacaatcca    5220
acctgctggg ccatctgcaa gagaatacca aacaaaaaac ctggaaagaa aaccaccacc    5280
aagcccacaa aaaaaccaac cctcaagaca accaaaaaag atcccaaacc tcaaaccaca    5340
aaaccaaagg aagtactcac taccaagcct acaggaaagc caaccatcaa caccactaaa    5400
acaaacatca gaactacact gctcacctcc aacaccaaag gaaatccaga acacacaagt    5460
caagaggaaa ccctccactc aaccacctcc gaaggctatc taagcccatc ccaagtctat    5520
acaacatccg gtcaagagga aaccctccac tcaaccacct ccgaaggcta tctaagccca    5580
tcacaagtct atacaacatc cgagtaccta tcacaatctc tatcttcatc caacacaaca    5640
aaatgatagt cattaaaaag cgtattgttg caaaaagcca tgaccaaatc aaacagaatc    5700
aaaatcaact ctggggcaaa taacaatgga gttgccaatc ctcaaaacaa atgctattac    5760
cacaatcctt gctgcagtca cactctgttt cgcttccagt caaaacatca ctgaagaatt    5820
ttatcaatca acatgcagtg cagttagcaa aggctatctt agtgctctaa gaactggttg    5880
gtatactagt gttataacta tagaattaag taatatcaag gaaataagt gtaatggtac    5940 agacgctaag gtaaaattaa taaaacaaga attagataaa tataaaaatg ctgtaacaga    6000
attgcagttg ctcatgcaaa gcacaccagc agccaacagt cgagccagaa gagaactacc    6060
aagatttatg aattatacac tcaacaatac caaaaacacc aatgtaacat taagtaagaa    6120
aaggaaaaga agatttcttg gattttttgtt aggtgttgga tctgcaatcg ccagtggcat    6180
tgccgtatcc aaggtcctgc acctagaagg ggaagtgaac aaaatcaaaa gtgctctact    6240
atccacaaac aaggctgtag tcagcttatc taatggagtc agtgtcttaa ccagcaaggt    6300
gttagacctc aaaaactata tagataaaca gttgttacct attgttaaca agcaaagctg    6360
cagcatatca aacattgaaa ctgtgataga gttccaacaa aagaacaaca gactactaga    6420
gattaccaga gaatttagtg ttaatgcagg tgtaactaca cctgtaagca cttatatgtt    6480
aactaatagt gagttattat cattaatcaa tgatatgcct ataacaaatg atcagaaaaa    6540
gttaatgtcc agcaatgttc aaatagttag acagcaaagt tactctatca tgtcaataat    6600
aaaagaggaa gtcttagcat atgtagtaca attaccacta tatggtgtaa tagatactcc    6660
ttgttggaaa ctacacacat ctcctctatg tacaaccaac acaaaggaag gatccaacat    6720
ctgcttaaca agaaccgaca gaggatggta ctgtgacaat gcaggatcag tatccttttt    6780
cccacaagct gaaacatgta aagttcaatc gaatcgggtg ttttgtgaca caatgaacag    6840
tttaacatta ccaagtgagg taaatctctg caacattgac atattcaacc ccaaatatga    6900
ttgcaaaatt atgacttcaa aaacagatgt aagcagctcc gttatcacat ctctaggagc    6960
cattgtgtca tgctatggca aaaccaaatg tacagcatcc aataaaaatc gtgggatcat    7020
```

-continued

```
aaagacattc tctaacgggt gtgattatgt atcaaataag ggggtggata ctgtgtctgt    7080
aggtaataca ttatattatg taaataagca agaaggcaaa agtctctatg taaaaggtga    7140
accaataata aatttctatg atccattagt gttcccctct gatgaatttg atgcatcaat    7200
atctcaagtc aatgagaaaa ttaatcagag tctagcattt atccgtaaat cagatgaatt    7260
attacataat gtaaatgctg gtaaatccac cacaaatatc atgataacta ccataattat    7320
agtaattata gtaatattgt tagcattaat tgcagttgga ctgcttctat actgcaaggc    7380
cagaagcaca ccagtcacat taggtaagga tcaactgagt ggtataaata atattgcatt    7440
taataactga ataaaaatag cacctaatca tattcttaca atggttcgct atttgaccat    7500
agataaccca tctatcatta gattatccta aaatttgaac ttcatcacaa ctttcatcta    7560
taaaccatct cacttacact ttttaagtag attcctattt tatagttata taaaacaatt    7620
gaataccaaa ttaacttact atttgtaaaa atgagaactg gggcaaatat gtcacgaagg    7680
aatccttgca aattcgaaat tcgaggtcat tgcttgaatg gtaaaaggtg tcattttagt    7740
cataattatt ttgaatggcc accccatgca ctgcttgtaa gacaaaactt tatgttaaac    7800
agaatactta agtctatgga taaaagcata gatactttgt cagaaataag tggagctgca    7860
gagttggaca gaacagaaga gtatgccctc ggtgtagttg gagtgctaga gagttatata    7920
ggatcaataa ataatataac taaacaatca gcatgtgttg ccatgagcaa actccttact    7980
gaactcaaca gcgatgacat caaaaaacta agggacaatg aagagccaaa ctcacccaaa    8040
gtaagagtgt acaatactgt catatcatat attgaaagca acaggaagaa caataaacaa    8100
actatccatc tgttaaaaag attgccagca gacgtattga agaaaaccat caaaaacaca    8160
ttggatatcc acaagagcat aaccatcaat aacccaaaag aatcaactgt tagtgatacg    8220
aacgaccatg ccaaaaataa tgatactacc tgacaaatat ccttgtagta taaattccat    8280
actaataaca agtaattgta gagtcactat gtataatcaa aaaaacacac tatatatcaa    8340 tcaaacaac caaaataacc atatataccc accggatcaa ccattcaatg aaatccattg    8400
gacctctcaa gacttgattg atgcaactca aaattttcta caacatctag gtattactga    8460
tgatatatac acaatatata tattagtgtc ataaactca atcctaatac ttaccacatc    8520
atcaaattat taactcaaac aattcaagct atgggacaaa atggatccca ttattagtgg    8580
aaattctgct aatgtttatc taactgatag ttatttaaaa ggtgttattt ctttctcaga    8640
atgtaacgct ttaggaagtt acatattcaa tggtccttat ctcaaaaatg attataccaa    8700
cttaattagt agacaaaatc cattaataga acacataaat ctaaagaaac taaatataac    8760
acagtcctta atatctaagt atcataaagg tgaaataaaa atagaagaac ctacttactt    8820
tcagtcatta cttatgacat acaagagtat gacctcgtca gaacgactac tactactaa    8880 tttacttaaa aagataataa gaagagctat agaaatcagt gatgtcaaag tctatgctat    8940
attgaataaa ctggggctca agaaaaaga caagattaaa tccaataatg gacaagatga    9000
agacaactca gtcattacta ccataatcaa agatgatata cttttagctg tcaaggataa    9060
tcaatctcat cttaaagcag acaaaaatca atccacaaaa caaaaagata caatcaaaac    9120 aacactttg aagaaattaa tgtgttcaat gcaacatcct ccatcatggt taatacattg    9180
gtttaattta tacacaaaat taaacagcat attaacacaa tatcgatcta gtgaggtaaa    9240
aaaccatggt tttatattga tagataatca tactcttagt ggattccaat ttattttgaa    9300
tcaatatggt tgtatagttt atcataagga actcaaaaga attactgtga caacttataa    9360
```

-continued

```
tcaattcttg acatggaaag atattagcct tagtagatta aatgtttgtt tgattacatg   9420
gattagtaac tgtttgaaca cattaaacaa aagcttaggc ttaagatgtg gattcaataa   9480
tgttatcttg acacaattat tcctttatgg agattgtata ctaaaactat tccacaatga   9540
ggggttctac ataataaaag agatagaggg atttattatg tctctaattt taaatataac   9600
agaagaagat caattcagaa aacggtttta taatagtatg ctcaacaaca tcacagatgc   9660
cgccaacaaa gctcaaaaaa atctgctatc aagagtatgt catacattat tagataagac   9720
aatatcagat aatataataa atggcagatg gataattcta ttgagcaagt tcctaaaatt   9780
aattaagctt gcaggtgaca ataacctcaa caatctgagt gaattatatt ttttgttcag   9840
gatatttgga cacccaatgg tagatgaaag acaagccatg gatgctgtta aagttaattg   9900
caacgagacc aaattttact tgttaagtag tttgagtatg ttaagaggag cttttatata   9960
tagaattata aaagggtttg taaataatta caacagatgg cctactttaa gaaatgccat  10020
tgtcttaccc ttaagatggt taacttacta taaactaaac acttatcctt ccttgttgga  10080
acttacagaa agagatttga ttgttctatc aggactacgt ttctatcgag agtttcggtt  10140
gcctaaaaaa gtggatcttg aaatgatcat aaatgataag gctatatcac ctcctaaaaa  10200
tttaatatgg actagtttcc ctagaaatta tatgccgtca cacatacaaa attatataga  10260
acatgaaaaa ttaaaattct ctgatagtga taaatcaaga agagtattag agtattattt  10320
aagagataac aaattcaatg aatgtgattt acacaactgt gtagttaatc aaagttatct  10380
taacaacccg aatcatgtgg tatcattgac aggcaaagaa agagaactca gtgtaggtag  10440
aatgtttgca atgcaaccag gaatgttcag acaagttcaa atattagcag agaaaatgat  10500
agcagaaaac atattacaat ttttccctga aagtcttaca agatatggtg atctagaact  10560
acagaaaata ttagaattga aagcaggaat aagtaacaaa tcaaatcgtt acaatgataa  10620
ttacaacaat tacattagta agtgctctat catcacagat ctcagcaaat tcaatcaagc  10680
atttcgatat gaaacatcat gtatttgtag tgatgtactg gatgaactgc atggtgtaca  10740
atctctattt tcctggttac atttaactat tcctcatgtc acaataatat gcacatatag  10800
gcatgcaccc ccctatataa aggatcatat tgtagatctt aacaatgtag atgagcaaag  10860
tggactatat agatatcata tgggtggtat cgaagggtgg tgtcaaaaac tatggactat  10920
agaagctata tcactattag atctaatatc tctcaaaggg aaattctcaa ttactgcttt  10980
aattaatggt gacaatcaat caatagatat aagtaaacca gtcagactca tggaaggtca  11040
aactcatgct caagcagatt atttgctagc attaaatagt ctcaaattac tgtataaaga  11100
gtatgcagga ataggccaca aattaaaagg aactgagact tatatatcga gagatatgca  11160
atttatgagt aaaacgatcc aacataacgg tgtatattac ccagctagta taaagaaagt  11220
cctaagagtg ggaccgtgga taaacactat acttgatgac ttcaaagtga gtctagaatc  11280
tataggtagt ttgacacaag aattagaata tagaggtgaa agtctattat gcagtttaat  11340
atttaggaat gtatggttat ataatcaaat tgcattacaa cttaaaaatc atgcattatg  11400
taacaacaaa ttatatttgg atatattaaa agttctaaaa cacttaaaaa ccttttttaa  11460
tcttgataac attgatacag cattaacatt gtatatgaat ttgcccatgt tatttggtgg  11520
tggtgatccc aacttgttat atcgaagttt ctatagaaga actcctgatt tcctcacaga  11580
ggctatagtt cactctgtgt tcatacttag ttattataca aaccatgatt aaaaagataa  11640
acttcaagat ctgtcagatg atagattgaa taagttctta acatgcataa tcacgtttga  11700
caaaaacccc aatgctgaat tcgttacatt gatgagagat cctcaagctt taggatctga  11760
```

-continued

```
gaggcaagct aaaattacta gcgaaatcaa tagactggca gttaccgagg tttttgagcac   11820 agctccaaac aaaatatttt ccaaaagtgc acaacactat accactacag agatagatct   11880
taatgatatt atgcaaaata tagaacctac atatcctcac gggttaagag ttgtttatga   11940
aagtttaccc ttttataaag cagagaaaat agtaaatctt atatccggta caaaatctat   12000
aactaacata ctggaaaaga cttctgccat agacttaaca gatattgata gagccactga   12060
gatgatgagg aaaaacataa ctttgcttat aaggatatta ccattagatt gtaacagaga   12120
taaaagagaa atattgagta tggaaaacct aagtattact gaattaagca aatacgttag   12180
agaaagatct tggtctttat ccaatatagt tggtgttaca tcacccagta tcatgtatac   12240
aatggacata aaatatacaa caagcactat agctagtggc ataatcatag agaaatataa   12300
tgtcaacagt ttaacacgtg gtgagagagg acccactaaa ccatgggttg gttcatctac   12360
acaagagaaa aagacaatgc cagtttataa tagacaagtt ttaaccaaaa aacagagaga   12420
tcaaatagat ctattagcaa aattggattg ggtgtatgca tctatagata acaaggatga   12480
atttatggag gaacttagca taggaactct tgggttaaca tatgagaagg ccaaaaaatt   12540
attcccacaa tatttaagtg ttaactattt gcatcgtctt acagtcagta gtagaccatg   12600
tgaattccct gcatctatac cagcttatag aactacaaat tatcactttg atactagccc   12660
tattaatcgc atattaacag aaaagtatgg tgatgaagat attgatatag tattccaaaa   12720
ctgtataagc tttggcctta gcttaatgtc tgtagtagaa caatttacta atgtgtgtcc   12780
taacagaatt attctcatac ccaagcttaa tgagatacat ttgatgaaac ctcccatatt   12840
cacaggtgat gttgatattc acaagttaaa acaagtgata caaaaacaac atatgtttt   12900 accagacaaa ataagtttga ctcaatatgt ggaattattc ttaagtaata aaacactcaa   12960
atctggatct aatgttaatt ctaatttaat attggcgcat aagatatctg actatttca   13020 taatacttac atttttaagta ctaatttagc tggacattgg attcttatta tacaacttat   13080
gaaagattct aagggtattt ttgaaaaaga ttggggagag ggatatataa ctgatcatat   13140
gttcattaat ttgaaagttt tcttcaatgc ttataagaca tatctcttgt gttttcataa   13200
aggttacggc agagcaaagc tggagtgtga tatgaatact tcagatctcc tatgtgtatt   13260
ggaattaata gacagtagtt attggaagtc tatgtctaag gtgttttag aacaaaaagt   13320 tatcaaatac attcttagcc aggatgcaag tttacataga gtaaaaggat gtcatagctt   13380
caaactatgg tttcttaaac gtcttaatgt agcagaattc acggtttgcc cttgggttgt   13440
taacatagat tatcatccaa cacatatgaa agcaatatta acttatattg atcttgttag   13500
aatgggattg ataaatatag atagaatata cattaaaaat aaacacaagt tcaatgatga   13560
gttttatact tctaatctgt tttacattaa ttataacttc tcagataata ctcatctatt   13620
aactaaacat ataaggattg ctaattccga attagaaagt aattacaaca aattatatca   13680
tcccacacca gaaaccctag aaaatatact aaccaatccg gttaaaagta atggaaaaaa   13740
gacactgagt gactattgta taggtaaaaa tgttgactca ataatgttac catcgttatc   13800
taataagaag cttattaaat cgtctacaat gattagaacc aattgcagca gacaagattt   13860
gtataattta tttcctacgg ttgtgattga taaaattata gatcattcag gyaatacagc   13920
caaatctaac caactttaca ctactacttc tcatcaaata tccttagtgc acaatagcac   13980
atcactttat tgcatgcttc cttggcatca tattaataga ttcaatttttg tatttagttc   14040 tacaggttgt aaaaattagta tagagtatat tttaaaagat cttaaaatta aggatcctaa   14100
```

-continued

```
ttgtatagca ttcataggtg aaggagcagg gaatttatta ttgcgtacag tagtggaact     14160
tcatcctgat ataagatata tttacagaag tctgaaagat tgcaatgatc atagtttacc     14220
aattgagttt ttaaggctgt acaatggaca tatcaacatt gattatggtg aaaatttgac     14280
cattcctgct acagatgcaa ccaacaacat tcattggtct tatttacata taaagtttgc     14340
tgaacctatc agtctttttg tctgtgatgc tgaattgcct gtaacagtca actggagtaa     14400
gattataata gagtggagca agcatgtaag aaaatgcaag tactgttctt cagttaataa     14460
atgtacatta atagtaaaat atcatgctca agatgatatc gatttcaaat tagacaacat     14520
aactatatta aaaacttatg tatgcttagg cagtaagtta aagggatctg aagtttactt     14580
agtccttaca ataggtcctg caaatgtgtt cccagtattt aatgtagcac aaaatgctaa     14640
attgatacta tcaagaacca aaaatttcat catgcctaaa aaagctgata agagtctat      14700 tgatgcaaat attaagagtt tgataccctt tcttgttac cctataacaa aaaaaggaat      14760
taataccgca ttgtctaaat taaagagtgt tgttagtgga gatatactat catattctat     14820
agctggacgt aatgaagttt tcagcaataa acttataaat cataagcata tgaacatctt     14880
aaagtggttc aatcatgttt taaatttcag atcaacagaa ttaaactata atcatttata     14940
tatggtagaa tctacttatc ctcatctaag tgaattgtta aacagcttga ctaccaatga     15000
acttaaaaaa ctgattaaaa tcacaggtag tttgttatac aacttttata atgaataatg     15060
agcaaaaatc ttataacaaa aatagctaca cactaacatt gtattcaatt atagttattt     15120
aaaattaata attatataat ttttaataac ttctagtgaa ctaatcctaa aattatcatt     15180
ttgatctagg aagaataagt ttaaatccaa atctaattgg tttatatgta tattaactaa     15240
attacgagat attagttttt gacacttttt ttctcgt                              15277
```

<210> SEQ ID NO 2
<211> LENGTH: 139
<212> TYPE: PRT
<213> ORGANISM: Human Respiratory Syncytial Virus

<400> SEQUENCE: 2

```
Met Gly Ser Asn Ser Leu Ser Met Ile Lys Val Arg Leu Gln Asn Leu
1               5                   10                  15

Phe Asp Asn Asp Glu Val Ala Leu Leu Lys Ile Thr Cys Tyr Thr Asp
            20                  25                  30

Lys Leu Ile Gln Leu Thr Asn Ala Leu Ala Lys Ala Val Ile His Thr
        35                  40                  45

Ile Lys Leu Asn Gly Ile Val Phe Val His Val Ile Thr Ser Ser Asp
    50                  55                  60

Ile Cys Pro Asn Asn Asn Ile Val Val Lys Ser Asn Phe Thr Thr Met
65                  70                  75                  80

Pro Val Leu Gln Asn Gly Gly Tyr Ile Trp Glu Met Met Glu Leu Thr
                85                  90                  95

His Cys Ser Gln Pro Asn Gly Leu Ile Asp Asp Asn Cys Glu Ile Lys
            100                 105                 110

Phe Ser Lys Lys Leu Ser Asp Ser Thr Met Thr Asn Tyr Met Asn Gln
        115                 120                 125

Leu Ser Glu Leu Leu Gly Phe Asp Leu Asn Pro
    130                 135
```

<210> SEQ ID NO 3
<211> LENGTH: 124
<212> TYPE: PRT

-continued

<213> ORGANISM: Human Respiratory Syncytial Virus

<400> SEQUENCE: 3

```
Met Asp Thr Thr His Asn Asp Thr Thr Pro Gln Arg Leu Met Ile Thr
1               5                   10                  15

Asp Met Arg Pro Leu Ser Leu Glu Thr Ile Ile Thr Ser Leu Thr Arg
            20                  25                  30

Asp Ile Ile Thr His Lys Phe Ile Tyr Leu Ile Asn His Glu Cys Ile
        35                  40                  45

Val Arg Lys Leu Asp Glu Arg Gln Ala Thr Phe Thr Phe Leu Val Asn
    50                  55                  60

Tyr Glu Met Lys Leu Leu His Lys Val Gly Ser Thr Lys Tyr Lys Lys
65                  70                  75                  80

Tyr Thr Glu Tyr Asn Thr Lys Tyr Gly Thr Phe Pro Met Pro Ile Phe
                85                  90                  95

Ile Asn His Asp Gly Phe Leu Glu Cys Ile Gly Ile Lys Pro Thr Lys
            100                 105                 110

His Thr Pro Ile Ile Tyr Lys Tyr Asp Leu Asn Pro
            115                 120
```

<210> SEQ ID NO 4
<211> LENGTH: 391
<212> TYPE: PRT
<213> ORGANISM: Human Respiratory Syncytial Virus

<400> SEQUENCE: 4

```
Met Ala Pro Ser Lys Val Lys Leu Asn Asp Thr Leu Asn Lys Asp Gln
1               5                   10                  15

Pro Pro Ser Ser Ser Lys Tyr Thr Ile Gln Arg Ser Thr Gly Asp Ser
            20                  25                  30

Thr Asp Thr Pro Asn Tyr Asp Val Gln Lys His Thr Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Lys Asp Ala Gly Tyr His Val Lys Ala Asn Gly Val Asp
                85                  90                  95

Val Thr Thr His Arg Gln Asp Ile Asn Gly Lys Glu Met Lys Phe Glu
            100                 105                 110

Val Leu Thr Leu Ala Ser Leu Thr Thr Glu Ile Gln Ile Asn Ile Glu
            115                 120                 125

Ile Glu Ser Arg Lys Ser Tyr Lys Lys Met Leu Lys Glu Met Gly Glu
        130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
            180                 185                 190

Glu Met Lys Arg Tyr Lys Gly Leu Leu Pro Lys Asp Ile Ala Asn Ser
            195                 200                 205

Phe Tyr Glu Val Phe Glu Lys Tyr Pro His Phe Ile Asp Val Phe Val
    210                 215                 220

His Phe Gly Ile Ala Gln Ser Ser Thr Arg Gly Gly Ser Arg Val Glu
```

-continued

```
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
                260                 265                 270

Gly His Ala Ser Val Gln Ala Glu Met Glu Gln Val Val Glu Val Tyr
                275                 280                 285

Glu Tyr Ala Gln Lys Leu Gly Gly Glu Ala Gly Phe Tyr His Ile Leu
        290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
                340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
    370                 375                 380

Lys Asp Asn Asp Val Glu Leu
385                 390

<210> SEQ ID NO 5
<211> LENGTH: 241
<212> TYPE: PRT
<213> ORGANISM: Human Respiratory Syncytial Virus

<400> SEQUENCE: 5

Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
                20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Asn Ser Thr Ile Ile Asn
    50                  55                  60

Pro Ile Asn Glu Thr Asp Asp Thr Val Gly Asn Lys Pro Asn Tyr Gln
65                  70                  75                  80

Arg Lys Pro Leu Val Ser Phe Lys Glu Asp Pro Thr Pro Ser Asp Asn
                85                  90                  95

Pro Phe Ser Lys Leu Tyr Lys Glu Thr Ile Glu Thr Phe Asp Asn Asn
                100                 105                 110

Glu Glu Glu Ser Ser Tyr Ser Tyr Glu Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Val Gly Leu Arg Glu Glu
                165                 170                 175

Met Ile Glu Lys Ile Arg Thr Glu Ala Leu Met Thr Asn Asp Arg Leu
                180                 185                 190

Glu Ala Met Ala Arg Leu Arg Asn Glu Glu Ser Glu Lys Met Ala Lys
        195                 200                 205
```

-continued

```
Asp Thr Ser Asp Glu Val Ser Leu Asn Pro Thr Ser Glu Lys Leu Asn
210                 215                 220

Asn Leu Leu Glu Gly Asn Asp Ser Asp Asn Asp Leu Ser Leu Glu Asp
225                 230                 235                 240

Phe

<210> SEQ ID NO 6
<211> LENGTH: 256
<212> TYPE: PRT
<213> ORGANISM: Human Respiratory Syncytial Virus

<400> SEQUENCE: 6

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
                20                  25                  30

Thr Ile Trp Val Pro Met Phe Gln Ser Ser Met Pro Ala Asp Leu Leu
            35                  40                  45

Ile Lys Glu Leu Ala Asn Val Asn Ile Leu Val Lys Gln Ile Ser Thr
        50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
                100                 105                 110

Lys Ala Cys Ser Leu Thr Cys Leu Lys Ser Lys Asn Met Leu Thr Thr
            115                 120                 125

Val Lys Asp Leu Thr Met Lys Thr Leu Asn Pro Thr His Asp Ile Ile
        130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
                180                 185                 190

Lys Ile Ile Pro Tyr Ser Gly Leu Leu Leu Val Ile Thr Val Thr Asp
            195                 200                 205

Asn Lys Gly Ala Phe Lys Tyr Ile Lys Pro Gln Ser Gln Phe Ile Val
        210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255

<210> SEQ ID NO 7
<211> LENGTH: 64
<212> TYPE: PRT
<213> ORGANISM: Human Respiratory Syncytial Virus

<400> SEQUENCE: 7

Met Glu Asn Thr Ser Ile Thr Ile Glu Phe Ser Ser Lys Phe Trp Pro
1               5                   10                  15

Tyr Phe Thr Leu Ile His Met Ile Thr Thr Ile Ile Ser Leu Ile Ile
                20                  25                  30

Ile Ile Ser Ile Met Ile Ala Ile Leu Asn Lys Leu Cys Glu Tyr Asn
```

-continued

```
                35                  40                  45
Val Phe His Asn Lys Thr Phe Glu Leu Pro Arg Ala Arg Val Asn Thr
    50                  55                  60

<210> SEQ ID NO 8
<211> LENGTH: 321
<212> TYPE: PRT
<213> ORGANISM: Human Respiratory Syncytial Virus

<400> SEQUENCE: 8

Met Ser Lys Thr Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Leu Thr Thr Ala Ile Ile Gln Asp Ala Thr
65                  70                  75                  80

Asn Gln Ile Lys Asn Thr Thr Pro Thr Tyr Leu Thr Gln Asn Pro Gln
                85                  90                  95

Leu Gly Ile Ser Phe Ser Asn Leu Ser Gly Thr Thr Ser Gln Ser Thr
            100                 105                 110

Thr Ile Leu Ala Ser Thr Thr Pro Ser Ala Glu Ser Thr Pro Gln Ser
        115                 120                 125

Thr Thr Val Lys Ile Lys Asn Thr Thr Thr Thr Gln Ile Leu Pro Ser
    130                 135                 140

Lys Pro Thr Thr Lys Gln Arg Gln Asn Lys Pro Gln Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Pro Lys Glu
    210                 215                 220

Val Leu Thr Thr Lys Pro Thr Gly Lys Pro Thr Ile Asn Thr Thr Lys
225                 230                 235                 240

Thr Asn Ile Arg Thr Thr Leu Leu Thr Ser Asn Thr Lys Gly Asn Pro
                245                 250                 255

Glu His Thr Ser Gln Glu Glu Thr Leu His Ser Thr Thr Ser Glu Gly
            260                 265                 270

Tyr Leu Ser Pro Ser Gln Val Tyr Thr Thr Ser Gly Gln Glu Glu Thr
        275                 280                 285

Leu His Ser Thr Thr Ser Glu Gly Tyr Leu Ser Pro Ser Gln Val Tyr
    290                 295                 300

Thr Thr Ser Glu Tyr Leu Ser Gln Ser Leu Ser Ser Ser Asn Thr Thr
305                 310                 315                 320

Lys

<210> SEQ ID NO 9
<211> LENGTH: 574
<212> TYPE: PRT
```

<213> ORGANISM: Human Respiratory Syncytial Virus

<400> SEQUENCE: 9

Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Ser Arg Ala Arg Arg Glu Leu Pro
                100                 105                 110

Arg Phe Met Asn Tyr Thr Leu Asn Asn Thr Lys Asn Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

-continued

```
Asp Val Ser Ser Ser Val Ile Thr Ser Leu Gly Ala Ile Val Ser Cys
            405             410             415

Tyr Gly Lys Thr Lys Cys Thr Ala Ser Asn Lys Asn Arg Gly Ile Ile
        420             425             430

Lys Thr Phe Ser Asn Gly Cys Asp Tyr Val Ser Asn Lys Gly Val Asp
        435             440             445

Thr Val Ser Val Gly Asn Thr Leu Tyr Tyr Val Asn Lys Gln Glu Gly
    450             455             460

Lys Ser Leu Tyr Val Lys Gly Glu Pro Ile Ile Asn Phe Tyr Asp Pro
465             470             475             480

Leu Val Phe Pro Ser Asp Glu Phe Asp Ala Ser Ile Ser Gln Val Asn
            485             490             495

Glu Lys Ile Asn Gln Ser Leu Ala Phe Ile Arg Lys Ser Asp Glu Leu
        500             505             510

Leu His Asn Val Asn Ala Gly Lys Ser Thr Thr Asn Ile Met Ile Thr
        515             520             525

Thr Ile Ile Ile Val Ile Ile Val Ile Leu Leu Ala Leu Ile Ala Val
    530             535             540

Gly Leu Leu Leu Tyr Cys Lys Ala Arg Ser Thr Pro Val Thr Leu Gly
545             550             555             560

Lys Asp Gln Leu Ser Gly Ile Asn Asn Ile Ala Phe Asn Asn
            565             570
```

```
<210> SEQ ID NO 10
<211> LENGTH: 194
<212> TYPE: PRT
<213> ORGANISM: Human Respiratory Syncytial Virus

<400> SEQUENCE: 10

Met Ser Arg Arg Asn Pro Cys Lys Phe Glu Ile Arg Gly His Cys Leu
1               5               10              15

Asn Gly Lys Arg Cys His Phe Ser His Asn Tyr Phe Glu Trp Pro Pro
            20              25              30

His Ala Leu Leu Val Arg Gln Asn Phe Met Leu Asn Arg Ile Leu Lys
        35              40              45

Ser Met Asp Lys Ser Ile Asp Thr Leu Ser Glu Ile Ser Gly Ala Ala
    50              55              60

Glu Leu Asp Arg Thr Glu Glu Tyr Ala Leu Gly Val Val Gly Val Leu
65              70              75              80

Glu Ser Tyr Ile Gly Ser Ile Asn Asn Ile Thr Lys Gln Ser Ala Cys
            85              90              95

Val Ala Met Ser Lys Leu Leu Thr Glu Leu Asn Ser Asp Asp Ile Lys
        100             105             110

Lys Leu Arg Asp Asn Glu Glu Pro Asn Ser Pro Lys Val Arg Val Tyr
        115             120             125

Asn Thr Val Ile Ser Tyr Ile Glu Ser Asn Arg Lys Asn Asn Lys Gln
    130             135             140

Thr Ile His Leu Leu Lys Arg Leu Pro Ala Asp Val Leu Lys Lys Thr
145             150             155             160

Ile Lys Asn Thr Leu Asp Ile His Lys Ser Ile Thr Ile Asn Asn Pro
            165             170             175

Lys Glu Ser Thr Val Ser Asp Thr Asn Asp His Ala Lys Asn Asn Asp
            180             185             190

Thr Thr
```

-continued

<210> SEQ ID NO 11
<211> LENGTH: 88
<212> TYPE: PRT
<213> ORGANISM: Human Respiratory Syncytial Virus

<400> SEQUENCE: 11

Met Pro Lys Ile Met Ile Leu Pro Asp Lys Tyr Pro Cys Ser Ile Asn
1               5                   10                  15

Ser Ile Leu Ile Thr Ser Asn Cys Arg Val Thr Met Tyr Asn Gln Lys
            20                  25                  30

Asn Thr Leu Tyr Ile Asn Gln Asn Asn Gln Asn Asn His Ile Tyr Pro
        35                  40                  45

Pro Asp Gln Pro Phe Asn Glu Ile His Trp Thr Ser Gln Asp Leu Ile
    50                  55                  60

Asp Ala Thr Gln Asn Phe Leu Gln His Leu Gly Ile Thr Asp Asp Ile
65                  70                  75                  80

Tyr Thr Ile Tyr Ile Leu Val Ser
                85

<210> SEQ ID NO 12
<211> LENGTH: 2165
<212> TYPE: PRT
<213> ORGANISM: Human Respiratory Syncytial Virus

<400> SEQUENCE: 12

Met Asp Pro Ile Ile Ser Gly Asn Ser Ala Asn Val Tyr Leu Thr Asp
1               5                   10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Ile Asn Leu Lys Lys Leu
    50                  55                  60

Asn Ile Thr Gln Ser Leu Ile Ser Lys Tyr His Lys Gly Glu Ile Lys
65                  70                  75                  80

Ile Glu Glu Pro Thr Tyr Phe Gln Ser Leu Leu Met Thr Tyr Lys Ser
                85                  90                  95

Met Thr Ser Ser Glu Gln Thr Thr Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140

Gln Asp Glu Asp Asn Ser Val Ile Thr Thr Ile Ile Lys Asp Asp Ile
145                 150                 155                 160

Leu Leu Ala Val Lys Asp Asn Gln Ser His Leu Lys Ala Asp Lys Asn
                165                 170                 175

Gln Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Ser Ile Leu Thr Gln Tyr Arg Ser Ser
    210                 215                 220

Glu Val Lys Asn His Gly Phe Ile Leu Ile Asp Asn His Thr Leu Ser
225                 230                 235                 240

-continued

```
Gly Phe Gln Phe Ile Leu Asn Gln Tyr Gly Cys Ile Val Tyr His Lys
            245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
            275                 280                 285

Ser Asn Cys Leu Asn Thr Leu Asn Lys Ser Leu Gly Leu Arg Cys Gly
        290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Ile Glu
                325                 330                 335

Gly Phe Ile Met Ser Leu Ile Leu Asn Ile Thr Glu Glu Asp Gln Phe
                340                 345                 350

Arg Lys Arg Phe Tyr Asn Ser Met Leu Asn Asn Ile Thr Asp Ala Ala
            355                 360                 365

Asn Lys Ala Gln Lys Asn Leu Leu Ser Arg Val Cys His Thr Leu Leu
        370                 375                 380

Asp Lys Thr Ile Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
                420                 425                 430

Met Val Asp Glu Arg Gln Ala Met Asp Ala Val Lys Val Asn Cys Asn
            435                 440                 445

Glu Thr Lys Phe Tyr Leu Leu Ser Ser Leu Ser Met Leu Arg Gly Ala
        450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
            515                 520                 525

Lys Lys Val Asp Leu Glu Met Ile Ile Asn Asp Lys Ala Ile Ser Pro
        530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Asp Ser
                565                 570                 575

Asp Lys Ser Arg Arg Val Leu Glu Tyr Tyr Leu Arg Asp Asn Lys Phe
            580                 585                 590

Asn Glu Cys Asp Leu His Asn Cys Val Val Asn Gln Ser Tyr Leu Asn
        595                 600                 605

Asn Pro Asn His Val Val Ser Leu Thr Gly Lys Glu Arg Glu Leu Ser
        610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
```

-continued

```
            660              665              670

Leu Lys Ala Gly Ile Ser Asn Lys Ser Asn Arg Tyr Asn Asp Asn Tyr
    675              680              685

Asn Asn Tyr Ile Ser Lys Cys Ser Ile Ile Thr Asp Leu Ser Lys Phe
    690              695              700

Asn Gln Ala Phe Arg Tyr Glu Thr Ser Cys Ile Cys Ser Asp Val Leu
705              710              715              720

Asp Glu Leu His Gly Val Gln Ser Leu Phe Ser Trp Leu His Leu Thr
                725              730              735

Ile Pro His Val Thr Ile Ile Cys Thr Tyr Arg His Ala Pro Pro Tyr
                740              745              750

Ile Lys Asp His Ile Val Asp Leu Asn Asn Val Asp Glu Gln Ser Gly
                755              760              765

Leu Tyr Arg Tyr His Met Gly Gly Ile Glu Gly Trp Cys Gln Lys Leu
    770              775              780

Trp Thr Ile Glu Ala Ile Ser Leu Leu Asp Leu Ile Ser Leu Lys Gly
785              790              795              800

Lys Phe Ser Ile Thr Ala Leu Ile Asn Gly Asp Asn Gln Ser Ile Asp
                805              810              815

Ile Ser Lys Pro Val Arg Leu Met Glu Gly Gln Thr His Ala Gln Ala
                820              825              830

Asp Tyr Leu Leu Ala Leu Asn Ser Leu Lys Leu Leu Tyr Lys Glu Tyr
                835              840              845

Ala Gly Ile Gly His Lys Leu Lys Gly Thr Glu Thr Tyr Ile Ser Arg
    850              855              860

Asp Met Gln Phe Met Ser Lys Thr Ile Gln His Asn Gly Val Tyr Tyr
865              870              875              880

Pro Ala Ser Ile Lys Lys Val Leu Arg Val Gly Pro Trp Ile Asn Thr
                885              890              895

Ile Leu Asp Asp Phe Lys Val Ser Leu Glu Ser Ile Gly Ser Leu Thr
                900              905              910

Gln Glu Leu Glu Tyr Arg Gly Glu Ser Leu Leu Cys Ser Leu Ile Phe
                915              920              925

Arg Asn Val Trp Leu Tyr Asn Gln Ile Ala Leu Gln Leu Lys Asn His
    930              935              940

Ala Leu Cys Asn Asn Lys Leu Tyr Leu Asp Ile Leu Lys Val Leu Lys
945              950              955              960

His Leu Lys Thr Phe Phe Asn Leu Asp Asn Ile Asp Thr Ala Leu Thr
                965              970              975

Leu Tyr Met Asn Leu Pro Met Leu Phe Gly Gly Gly Asp Pro Asn Leu
                980              985              990

Leu Tyr Arg Ser Phe Tyr Arg Arg  Thr Pro Asp Phe Leu  Thr Glu Ala
    995              1000              1005

Ile Val  His Ser Val Phe Ile  Leu Ser Tyr Tyr Thr  Asn His Asp
    1010              1015              1020

Leu Lys  Asp Lys Leu Gln Asp  Leu Ser Asp Asp Arg  Leu Asn Lys
    1025              1030              1035

Phe Leu  Thr Cys Ile Ile Thr  Phe Asp Lys Asn Pro  Asn Ala Glu
    1040              1045              1050

Phe Val  Thr Leu Met Arg Asp  Pro Gln Ala Leu Gly  Ser Glu Arg
    1055              1060              1065

Gln Ala  Lys Ile Thr Ser Glu  Ile Asn Arg Leu Ala  Val Thr Glu
    1070              1075              1080
```

-continued

```
Val Leu  Ser Thr Ala Pro Asn  Lys Ile Phe Ser Lys  Ser Ala Gln
    1085                1090                1095

His Tyr  Thr Thr Thr Glu Ile  Asp Leu Asn Asp Ile  Met Gln Asn
    1100                1105                1110

Ile Glu  Pro Thr Tyr Pro His  Gly Leu Arg Val Val  Tyr Glu Ser
    1115                1120                1125

Leu Pro  Phe Tyr Lys Ala Glu  Lys Ile Val Asn Leu  Ile Ser Gly
    1130                1135                1140

Thr Lys  Ser Ile Thr Asn Ile  Leu Glu Lys Thr Ser  Ala Ile Asp
    1145                1150                1155

Leu Thr  Asp Ile Asp Arg Ala  Thr Glu Met Met Arg  Lys Asn Ile
    1160                1165                1170

Thr Leu  Leu Ile Arg Ile Leu  Pro Leu Asp Cys Asn  Arg Asp Lys
    1175                1180                1185

Arg Glu  Ile Leu Ser Met Glu  Asn Leu Ser Ile Thr  Glu Leu Ser
    1190                1195                1200

Lys Tyr  Val Arg Glu Arg Ser  Trp Ser Leu Ser Asn  Ile Val Gly
    1205                1210                1215

Val Thr  Ser Pro Ser Ile Met  Tyr Thr Met Asp Ile  Lys Tyr Thr
    1220                1225                1230

Thr Ser  Thr Ile Ala Ser Gly  Ile Ile Ile Glu Lys  Tyr Asn Val
    1235                1240                1245

Asn Ser  Leu Thr Arg Gly Glu  Arg Gly Pro Thr Lys  Pro Trp Val
    1250                1255                1260

Gly Ser  Ser Thr Gln Glu Lys  Lys Thr Met Pro Val  Tyr Asn Arg
    1265                1270                1275

Gln Val  Leu Thr Lys Lys Gln  Arg Asp Gln Ile Asp  Leu Leu Ala
    1280                1285                1290

Lys Leu  Asp Trp Val Tyr Ala  Ser Ile Asp Asn Lys  Asp Glu Phe
    1295                1300                1305

Met Glu  Glu Leu Ser Ile Gly  Thr Leu Gly Leu Thr  Tyr Glu Lys
    1310                1315                1320

Ala Lys  Lys Leu Phe Pro Gln  Tyr Leu Ser Val Asn  Tyr Leu His
    1325                1330                1335

Arg Leu  Thr Val Ser Ser Arg  Pro Cys Glu Phe Pro  Ala Ser Ile
    1340                1345                1350

Pro Ala  Tyr Arg Thr Thr Asn  Tyr His Phe Asp Thr  Ser Pro Ile
    1355                1360                1365

Asn Arg  Ile Leu Thr Glu Lys  Tyr Gly Asp Glu Asp  Ile Asp Ile
    1370                1375                1380

Val Phe  Gln Asn Cys Ile Ser  Phe Gly Leu Ser Leu  Met Ser Val
    1385                1390                1395

Val Glu  Gln Phe Thr Asn Val  Cys Pro Asn Arg Ile  Ile Leu Ile
    1400                1405                1410

Pro Lys  Leu Asn Glu Ile His  Leu Met Lys Pro Pro  Ile Phe Thr
    1415                1420                1425

Gly Asp  Val Asp Ile His Lys  Leu Lys Gln Val Ile  Gln Lys Gln
    1430                1435                1440

His Met  Phe Leu Pro Asp Lys  Ile Ser Leu Thr Gln  Tyr Val Glu
    1445                1450                1455

Leu Phe  Leu Ser Asn Lys Thr  Leu Lys Ser Gly Ser  Asn Val Asn
    1460                1465                1470
```

-continued

```
Ser Asn Leu Ile Leu Ala His Lys Ile Ser Asp Tyr Phe His Asn
1475          1480          1485

Thr Tyr Ile Leu Ser Thr Asn Leu Ala Gly His Trp Ile Leu Ile
1490          1495          1500

Ile Gln Leu Met Lys Asp Ser Lys Gly Ile Phe Glu Lys Asp Trp
1505          1510          1515

Gly Glu Gly Tyr Ile Thr Asp His Met Phe Ile Asn Leu Lys Val
1520          1525          1530

Phe Phe Asn Ala Tyr Lys Thr Tyr Leu Leu Cys Phe His Lys Gly
1535          1540          1545

Tyr Gly Arg Ala Lys Leu Glu Cys Asp Met Asn Thr Ser Asp Leu
1550          1555          1560

Leu Cys Val Leu Glu Leu Ile Asp Ser Ser Tyr Trp Lys Ser Met
1565          1570          1575

Ser Lys Val Phe Leu Glu Gln Lys Val Ile Lys Tyr Ile Leu Ser
1580          1585          1590

Gln Asp Ala Ser Leu His Arg Val Lys Gly Cys His Ser Phe Lys
1595          1600          1605

Leu Trp Phe Leu Lys Arg Leu Asn Val Ala Glu Phe Thr Val Cys
1610          1615          1620

Pro Trp Val Val Asn Ile Asp Tyr His Pro Thr His Met Lys Ala
1625          1630          1635

Ile Leu Thr Tyr Ile Asp Leu Val Arg Met Gly Leu Ile Asn Ile
1640          1645          1650

Asp Arg Ile Tyr Ile Lys Asn Lys His Lys Phe Asn Asp Glu Phe
1655          1660          1665

Tyr Thr Ser Asn Leu Phe Tyr Ile Asn Tyr Asn Phe Ser Asp Asn
1670          1675          1680

Thr His Leu Leu Thr Lys His Ile Arg Ile Ala Asn Ser Glu Leu
1685          1690          1695

Glu Ser Asn Tyr Asn Lys Leu Tyr His Pro Thr Pro Glu Thr Leu
1700          1705          1710

Glu Asn Ile Leu Thr Asn Pro Val Lys Ser Asn Gly Lys Lys Thr
1715          1720          1725

Leu Ser Asp Tyr Cys Ile Gly Lys Asn Val Asp Ser Ile Met Leu
1730          1735          1740

Pro Ser Leu Ser Asn Lys Lys Leu Ile Lys Ser Ser Thr Met Ile
1745          1750          1755

Arg Thr Asn Cys Ser Arg Gln Asp Leu Tyr Asn Leu Phe Pro Thr
1760          1765          1770

Val Val Ile Asp Lys Ile Ile Asp His Ser Gly Asn Thr Ala Lys
1775          1780          1785

Ser Asn Gln Leu Tyr Thr Thr Thr Ser His Gln Ile Ser Leu Val
1790          1795          1800

His Asn Ser Thr Ser Leu Tyr Cys Met Leu Pro Trp His His Ile
1805          1810          1815

Asn Arg Phe Asn Phe Val Phe Ser Ser Thr Gly Cys Lys Ile Ser
1820          1825          1830

Ile Glu Tyr Ile Leu Lys Asp Leu Lys Ile Lys Asp Pro Asn Cys
1835          1840          1845

Ile Ala Phe Ile Gly Glu Gly Ala Gly Asn Leu Leu Leu Arg Thr
1850          1855          1860

Val Val Glu Leu His Pro Asp Ile Arg Tyr Ile Tyr Arg Ser Leu
```

-continued

```
              1865                    1870                    1875

Lys Asp  Cys Asn Asp His Ser  Leu Pro Ile Glu Phe  Leu Arg Leu
     1880                    1885                    1890

Tyr Asn  Gly His Ile Asn Ile  Asp Tyr Gly Glu Asn  Leu Thr Ile
     1895                    1900                    1905

Pro Ala  Thr Asp Ala Thr Asn  Asn Ile His Trp Ser  Tyr Leu His
     1910                    1915                    1920

Ile Lys  Phe Ala Glu Pro Ile  Ser Leu Phe Val Cys  Asp Ala Glu
     1925                    1930                    1935

Leu Pro  Val Thr Val Asn Trp  Ser Lys Ile Ile Ile  Glu Trp Ser
     1940                    1945                    1950

Lys His  Val Arg Lys Cys Lys  Tyr Cys Ser Ser Val  Asn Lys Cys
     1955                    1960                    1965

Thr Leu  Ile Val Lys Tyr His  Ala Gln Asp Asp Ile  Asp Phe Lys
     1970                    1975                    1980

Leu Asp  Asn Ile Thr Ile Leu  Lys Thr Tyr Val Cys  Leu Gly Ser
     1985                    1990                    1995

Lys Leu  Lys Gly Ser Glu Val  Tyr Leu Val Leu Thr  Ile Gly Pro
     2000                    2005                    2010

Ala Asn  Val Phe Pro Val Phe  Asn Val Ala Gln Asn  Ala Lys Leu
     2015                    2020                    2025

Ile Leu  Ser Arg Thr Lys Asn  Phe Ile Met Pro Lys  Lys Ala Asp
     2030                    2035                    2040

Lys Glu  Ser Ile Asp Ala Asn  Ile Lys Ser Leu Ile  Pro Phe Leu
     2045                    2050                    2055

Cys Tyr  Pro Ile Thr Lys Lys  Gly Ile Asn Thr Ala  Leu Ser Lys
     2060                    2065                    2070

Leu Lys  Ser Val Val Ser Gly  Asp Ile Leu Ser Tyr  Ser Ile Ala
     2075                    2080                    2085

Gly Arg  Asn Glu Val Phe Ser  Asn Lys Leu Ile Asn  His Lys His
     2090                    2095                    2100

Met Asn  Ile Leu Lys Trp Phe  Asn His Val Leu Asn  Phe Arg Ser
     2105                    2110                    2115

Thr Glu  Leu Asn Tyr Asn His  Leu Tyr Met Val Glu  Ser Thr Tyr
     2120                    2125                    2130

Pro His  Leu Ser Glu Leu Leu  Asn Ser Leu Thr Thr  Asn Glu Leu
     2135                    2140                    2145

Lys Lys  Leu Ile Lys Ile Thr  Gly Ser Leu Leu Tyr  Asn Phe Tyr
     2150                    2155                    2160

Asn Glu
     2165
```